(12) United States Patent
Clarke et al.

(10) Patent No.: US 8,101,244 B2
(45) Date of Patent: Jan. 24, 2012

(54) APPARATUS AND METHOD FOR PRODUCING OR PROCESSING A PRODUCT OR SAMPLE

(75) Inventors: Allan J. Clarke, Collegeville, PA (US); David George Doughty, Harlow (GB); Frederick H. Fiesser, King of Prussia, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 1126 days.

(21) Appl. No.: 11/148,822

(22) Filed: Jun. 9, 2005

(65) Prior Publication Data

US 2006/0001866 A1 Jan. 5, 2006

Related U.S. Application Data

(60) Provisional application No. 60/621,992, filed on Oct. 25, 2004, provisional application No. 60/578,245, filed on Jun. 9, 2004.

(51) Int. Cl.
*B05C 11/10* (2006.01)

(52) U.S. Cl. ........ 427/427.2; 118/666; 118/687; 118/712; 118/713; 347/19

(58) Field of Classification Search ........ 118/665, 118/666, 667, 679, 712, 713, 669, 686, 687; 222/55; 347/19; 427/9, 10, 427.2
See application file for complete search history.

(56) References Cited

U.S. PATENT DOCUMENTS

| | | | |
|---|---|---|---|
| 3,834,590 A | 9/1974 | Robinson et al. | 73/864.17 |
| 3,884,143 A | 5/1975 | Ackley | 101/37 |
| 3,923,207 A | 12/1975 | Kyogoku | 222/386 |
| 4,006,578 A | 2/1977 | Gamberini | |
| 4,197,289 A | 4/1980 | Sturzenegger et al. | 424/21 |
| 4,205,384 A | 5/1980 | Merz et al. | |
| 4,257,267 A | 3/1981 | Parsons | 73/864.14 |
| 4,349,531 A | 9/1982 | Mlodozeniec et al. | |
| 4,397,556 A | 8/1983 | Muller | |
| 4,408,641 A | 10/1983 | Yamamoto et al. | |
| 4,450,877 A | 5/1984 | Walker et al. | |
| 4,485,387 A | 11/1984 | Drumheller | 346/140.1 |
| 4,489,026 A | 12/1984 | Yalkowsky | 264/123 |
| 4,545,412 A | 10/1985 | Gamberini | |

(Continued)

FOREIGN PATENT DOCUMENTS

BG 63143 5/2001

(Continued)

OTHER PUBLICATIONS

Chiarello, K., Fingerprinting Technology Combats Counterfeit Drugs, Aug. 2004, p. 15, Pharmaceutical Technology (Complete Article).

(Continued)

*Primary Examiner* — George R Koch, III

(74) *Attorney, Agent, or Firm* — Ohlandt, Greeley, Ruggiero & Perle, LLP

(57) ABSTRACT

An apparatus and method are provided for producing a plurality of products or processing a plurality of samples via dispensing. The apparatus and method provide real-time monitoring of the products/samples and can provide real-time control. The apparatus and method can monitor the liquid both before and after it has been added to a carrier substrate. The apparatus and method can provide monitoring of each product/sample that is processed.

26 Claims, 13 Drawing Sheets

U.S. PATENT DOCUMENTS

| | | | |
|---|---|---|---|
| 4,548,825 A | 10/1985 | Voss et al. | 426/383 |
| 4,784,582 A | 11/1988 | Howseman | |
| 4,866,906 A | 9/1989 | Tayebi | |
| 4,867,099 A | 9/1989 | Heine et al. | 118/630 |
| 4,927,062 A | 5/1990 | Walsh | 222/420 |
| 4,936,828 A | 6/1990 | Chiang | |
| 4,978,859 A | 12/1990 | Karsheim | |
| 5,040,353 A | 8/1991 | Evans et al. | 53/54 |
| 5,085,510 A | 2/1992 | Mitchell | |
| 5,195,656 A | 3/1993 | Briehl et al. | 222/1 |
| 5,223,225 A | 6/1993 | Gautsch | 422/100 |
| 5,278,626 A | 1/1994 | Poole et al. | |
| 5,312,233 A | 5/1994 | Tanny et al. | 417/316 |
| 5,324,359 A | 6/1994 | Cleveland | |
| 5,334,353 A | 8/1994 | Blattner | 422/100 |
| 5,442,892 A | 8/1995 | Burns et al. | 53/53 |
| 5,525,515 A | 6/1996 | Blattner | 436/49 |
| 5,588,963 A | 12/1996 | Roelofs | |
| 5,593,290 A | 1/1997 | Greisch et al. | 417/478 |
| 5,656,080 A | 8/1997 | Staniforth et al. | 118/20 |
| 5,711,989 A * | 1/1998 | Ciardella et al. | 427/8 |
| 5,753,302 A | 5/1998 | Sun et al. | |
| 5,799,468 A | 9/1998 | Eck et al. | 53/453 |
| 5,810,988 A | 9/1998 | Smith et al. | 204/666 |
| 5,856,200 A | 1/1999 | Krause et al. | |
| 5,900,634 A | 5/1999 | Soloman | |
| 5,906,682 A * | 5/1999 | Bouras et al. | 118/712 |
| 5,916,524 A | 6/1999 | Tisone | 422/100 |
| 5,964,381 A | 10/1999 | El-Hage et al. | 222/386 |
| 5,973,324 A | 10/1999 | Saby | |
| 5,997,518 A | 12/1999 | Laibovitz et al. | 604/296 |
| 6,149,815 A | 11/2000 | Sauter et al. | 210/635 |
| 6,159,186 A | 12/2000 | Wickham et al. | |
| 6,176,277 B1 | 1/2001 | Mayer | |
| 6,213,354 B1 | 4/2001 | Kay | |
| 6,345,717 B1 | 2/2002 | Flewitt | 206/531 |
| 6,479,994 B1 | 11/2002 | Hills et al. | 324/306 |
| 6,063,194 A1 | 1/2003 | Poliniak et al. | |
| 6,509,537 B1 | 1/2003 | Krieg et al. | 209/579 |
| 6,540,833 B1 * | 4/2003 | Gibson et al. | 118/410 |
| 6,561,224 B1 | 5/2003 | Cho | 137/827 |
| 6,592,932 B2 * | 7/2003 | Subramanian et al. | 427/10 |
| 6,623,785 B2 | 9/2003 | Childers | 427/2.14 |
| 6,667,802 B2 | 12/2003 | Faus et al. | |
| 6,690,464 B1 | 2/2004 | Lewis et al. | |
| 6,702,894 B2 | 3/2004 | Lee et al. | |
| 6,765,212 B2 | 7/2004 | Goetz et al. | |
| 6,772,801 B1 | 8/2004 | Shojaei et al. | |
| 6,786,579 B2 | 9/2004 | Noolandi et al. | |
| 6,791,688 B2 | 9/2004 | Lai et al. | 356/417 |
| 6,919,556 B1 | 7/2005 | Laurence | |
| 6,946,157 B2 | 9/2005 | Folestad et al. | 427/2.15 |
| 6,962,715 B2 | 11/2005 | Lee et al. | |
| 7,083,937 B2 | 8/2006 | Sasisekharan et al. | |
| 7,118,010 B2 | 10/2006 | Crowder et al. | |
| 7,154,102 B2 * | 12/2006 | Poteet et al. | 250/372 |
| 7,182,959 B2 | 2/2007 | Martani | |
| 7,247,338 B2 | 7/2007 | Pui et al. | 427/2.14 |
| 2001/0011197 A1 * | 8/2001 | White | 700/96 |
| 2001/0050294 A1 | 12/2001 | Plattner et al. | |
| 2002/0001675 A1 | 1/2002 | Tisone | 427/256 |
| 2002/0034592 A1 | 3/2002 | Hogan | |
| 2002/0079325 A1 * | 6/2002 | Estelle | 222/1 |
| 2002/0081236 A1 | 6/2002 | Bass et al. | 435/6 |
| 2002/0100770 A1 | 8/2002 | Strecker | 222/145.1 |
| 2002/0110641 A1 | 8/2002 | Tanaka et al. | 427/240 |
| 2002/0131998 A1 | 9/2002 | Martani | |
| 2002/0136822 A1 | 9/2002 | Folestad et al. | |
| 2002/0169143 A1 | 11/2002 | Sasisekharan | |
| 2002/0173669 A1 | 11/2002 | Schultz et al. | |
| 2002/0187248 A1 | 12/2002 | Childers | 427/2.1 |
| 2002/0187564 A1 | 12/2002 | Chow et al. | 436/169 |
| 2003/0008386 A1 | 1/2003 | Bass et al. | 435/6 |
| 2003/0032198 A1 | 2/2003 | Lugmair et al. | 436/180 |
| 2003/0054025 A1 | 3/2003 | Cantor et al. | 424/449 |
| 2003/0056722 A1 | 3/2003 | Kitano et al. | 118/323 |
| 2003/0065294 A1 | 4/2003 | Pickup et al. | 604/305 |
| 2003/0075106 A1 | 4/2003 | Lee et al. | 118/325 |
| 2003/0077315 A1 | 4/2003 | Lee et al. | 424/439 |
| 2003/0080208 A1 | 5/2003 | Williams et al. | 239/290 |
| 2003/0099708 A1 | 5/2003 | Rowe et al. | |
| 2003/0101991 A1 | 6/2003 | Trueba | 128/200.16 |
| 2003/0143315 A1 | 7/2003 | Pui et al. | |
| 2003/0145750 A1 * | 8/2003 | Chang et al. | 101/484 |
| 2003/0147952 A1 | 8/2003 | Lim et al. | 424/464 |
| 2003/0175410 A1 | 9/2003 | Campbell et al. | 427/2.24 |
| 2003/0189115 A1 | 10/2003 | Klaseboer et al. | 239/690 |
| 2003/0228242 A1 | 12/2003 | Feygin | 141/234 |
| 2004/0005360 A1 | 1/2004 | Wang et al. | |
| 2004/0028732 A1 | 2/2004 | Falkenhausen et al. | |
| 2004/0081689 A1 | 4/2004 | Danfield et al. | |
| 2004/0099159 A1 | 5/2004 | Volder | |
| 2004/0119795 A1 | 6/2004 | Noolandi et al. | |
| 2004/0135086 A1 | 7/2004 | Lewis et al. | |
| 2004/0137140 A1 | 7/2004 | Childers | |
| 2004/0154534 A1 | 8/2004 | Lee et al. | |
| 2004/0172169 A1 | 9/2004 | Wright et al. | |
| 2004/0231594 A1 * | 11/2004 | Edwards et al. | 118/719 |
| 2004/0256453 A1 | 12/2004 | Lammle | 235/381 |
| 2004/0261700 A1 * | 12/2004 | Edwards et al. | 118/679 |
| 2005/0000422 A1 | 1/2005 | Edwards et al. | |
| 2005/0016451 A1 | 1/2005 | Edwards et al. | |
| 2005/0077476 A1 | 4/2005 | Poteet et al. | |
| 2005/0118246 A1 | 6/2005 | Wong et al. | |
| 2005/0129746 A1 | 6/2005 | Lee et al. | |
| 2005/0186253 A1 | 8/2005 | Lee et al. | 424/439 |
| 2005/0199788 A1 | 9/2005 | Lewis et al. | 250/226 |
| 2005/0233000 A1 | 10/2005 | Figueroa et al. | |
| 2005/0238697 A1 | 10/2005 | Chinea et al. | |
| 2005/0257738 A1 | 11/2005 | Tateishi et al. | |
| 2006/0008507 A1 | 1/2006 | Gore | |
| 2006/0018969 A1 | 1/2006 | Figueroa et al. | |
| 2006/0144331 A1 | 7/2006 | Hanafusa et al. | |
| 2006/0156120 A1 | 7/2006 | Kim | |
| 2006/0160238 A1 | 7/2006 | Lemernas | |
| 2006/0172060 A1 | 8/2006 | Teichman et al. | |
| 2006/0184043 A1 | 8/2006 | Tromberg et al. | |
| 2006/0190137 A1 | 8/2006 | Free | |
| 2006/0195270 A1 | 8/2006 | Charlton | |
| 2006/0282223 A1 | 12/2006 | Neil et al. | |
| 2007/0035567 A1 | 2/2007 | Kim et al. | |
| 2007/0056511 A1 | 3/2007 | Childers | |
| 2007/0060564 A1 | 3/2007 | But et al. | |

FOREIGN PATENT DOCUMENTS

| | | |
|---|---|---|
| DE | 2658486 | 6/1978 |
| DE | 2849495 | 5/1980 |
| DE | 3239955 | 5/1984 |
| DE | 3246453 | 6/1984 |
| DE | 4203273 | 8/1992 |
| DE | 2244968 | 8/1993 |
| DE | 19535010 | 3/1997 |
| DE | 19852947 | 5/2000 |
| DE | 19930729 | 1/2001 |
| DE | 19940241 | 3/2001 |
| DE | 19940242 | 3/2001 |
| DE | 19955240 | 5/2001 |
| DE | 10121471 | 11/2002 |
| EP | 11268 | 5/1980 |
| EP | 24230 | 2/1981 |
| EP | 127267 | 12/1984 |
| EP | 224930 | 6/1987 |
| EP | 303025 | 2/1989 |
| EP | 0596328 | 5/1994 |
| EP | 788790 | 8/1997 |
| EP | 810438 | 12/1997 |
| EP | 915014 | 5/1999 |
| EP | 950520 | 10/1999 |
| EP | 1099484 | 5/2001 |
| EP | 1150105 | 10/2001 |
| EP | 1206966 | 5/2002 |
| EP | 1306219 | 5/2003 |
| FR | 2674747 | 10/1992 |
| GB | 310855 | 10/1930 |
| GB | 2377661 | 1/2003 |
| JP | 57179712 | 11/1982 |
| JP | 63177022 | 7/1988 |

| | | |
|---|---|---|
| JP | 05124954 | 5/1993 |
| JP | 10264411 | 10/1998 |
| JP | 11128345 | 5/1999 |
| JP | 11337557 | 12/1999 |
| JP | 2000/042089 | 2/2000 |
| JP | 2000/185106 | 7/2000 |
| JP | 2001/213765 | 8/2001 |
| JP | 2001/232178 | 8/2001 |
| JP | 2004/041464 | 2/2004 |
| JP | 2004-69484 | 3/2004 |
| SU | 952254 | 8/1982 |
| TW | 419376 | 1/2001 |
| WO | WO 8301053 | 3/1983 |
| WO | WO 8702241 | 4/1987 |
| WO | WO 8907429 | 8/1989 |
| WO | WO 9222800 | 12/1992 |
| WO | WO 9511007 | 4/1995 |
| WO | WO 9734138 | 9/1997 |
| WO | WO 9744134 | 11/1997 |
| WO | WO 9748384 | 12/1997 |
| WO | WO 9800107 | 1/1998 |
| WO | WO 9820861 | 5/1998 |
| WO | WO 9836738 | 8/1998 |
| WO | WO 9836739 | 8/1998 |
| WO | WO 9843762 | 10/1998 |
| WO | WO 9845205 | 10/1998 |
| WO | WO 9857747 | 12/1998 |
| WO | WO 9911373 | 3/1999 |
| WO | WO 9931468 | 6/1999 |
| WO | WO 9936176 | 7/1999 |
| WO | WO 99/63972 | 12/1999 |
| WO | WO 9965704 | 12/1999 |
| WO | WO 00/33087 | 6/2000 |
| WO | WO 00/41723 | 7/2000 |
| WO | WO 00/45051 | 8/2000 |
| WO | WO 00/56463 | 9/2000 |
| WO | WO 00/65352 | 11/2000 |
| WO | WO 01/07354 | 2/2001 |
| WO | WO 01/12327 | 2/2001 |
| WO | WO 01/30573 | 5/2001 |
| WO | WO 01/50877 | 7/2001 |
| WO | WO 01/64345 | 9/2001 |
| WO | WO 01/87272 | 11/2001 |
| WO | WO 02/03966 | 1/2002 |
| WO | WO 02/28534 | 4/2002 |
| WO | WO 02/37096 | 5/2002 |
| WO | WO 02/38280 | 5/2002 |
| WO | WO 02/40165 | 5/2002 |
| WO | WO 02/40273 | 5/2002 |
| WO | WO 02/43845 | 6/2002 |
| WO | WO 02/055199 | 7/2002 |
| WO | WO 02/082024 | 10/2002 |
| WO | WO 02/085521 | 10/2002 |
| WO | WO 02/097445 | 12/2002 |
| WO | WO 02/102514 | 12/2002 |
| WO | WO 02/102515 | 12/2002 |
| WO | WO 03/006177 | 1/2003 |
| WO | WO 03/016832 | 2/2003 |
| WO | WO 03/023410 | 3/2003 |
| WO | WO 03/023692 | 3/2003 |
| WO | WO 03/024596 | 3/2003 |
| WO | WO 03/037244 | 5/2003 |
| WO | WO 03/037607 | 5/2003 |
| WO | WO 03/037632 | 5/2003 |
| WO | WO 03/041690 | 5/2003 |
| WO | WO 03/048665 | 6/2003 |
| WO | WO 03/053582 | 7/2003 |
| WO | WO 03/092633 | 11/2003 |
| WO | WO 2004/005014 | 1/2004 |
| WO | WO 2004/049466 | 6/2004 |

OTHER PUBLICATIONS de Gans et al. Inkjet Printing of Polymers: State of the Art and Future Developments (Review), Feb. 3, 2004, 16(3), pp. 203-213, Advanced Materials (Abstract).

Dhiman, M., Designing of Modified Release Tablets, 2003, vol. 2, pp. 25-30, Indian Pharmacist (Abstract).

Lee et al., Evaluation of Critical Formulation Factors in the Development of a Rapidly Dispersing Captopril Oral Dosage Form, 2003, 29(9), pp. 967-979, Drug Development & Industrial Pharmacy (Abstract).

Meng et al., Polymer MEMS for Micro Fluid Delivery Systems, Sep. 7-11, 2003, Abstracts of Papers, 226$^{th}$ ACS National Meeting, New York, NY, United States (Abstract).

Rowe et al., Theriform Technology, 2003, pp. 77-87, Drugs and the Pharmaceutical Sciences (Abstract).

Yoon et al., A New Process for Making Reservoir-Type Microcapsules Using Ink-Jet Technology and Interfacial Phase Separation, Dec. 5, 2003, 93(2), pp. 161-173, Journal of Controlled Release (Abstract).

Gooray et al., Design of a MEMS Ejector for Printing Applications, Sep.-Oct. 2002, 46(5), pp. 415-421, Journal of Imaging Science & Technology (Abstract).

Griss et al., Expandable Microspheres for the Handling of Liquids, May 2002, vol. 2, No. 2, pp. 117-120, Lab on a Chip (Abstract).

Held, P., The µFill: A New 96-/384- Wellmicroplate Reagent Dispenser for HTS and Drug Discovery, 2002, 7/3, pp. 84, Journal of the Association for Laboratory Automation (Abstract).

Howard et al., Ink-Jet Printer Heads for Ultra-Small-Drop Protien Crystallography, Dec. 2002, 33(6), pp. 1302+, Biotechniques (Abstract).

Kuil et al., Protien Nano-Crystallogenesis, Mar. 13, 2002, 30(3), pp. 262-265, Enzyme and Microbial Technology (Abstract).

Puntambekar et al., Fixed-Volume Metering Microdispenser Module, 2002, 2(4), pp. 213-218, Lab on a Chip (Abstract).

Puntamaker et al., 3-D Microfluidic Networks for Combinational Chemistry, Nov. 3-7, 2002, vol. 1, pp. 422-424, Micro Total Analysis Systems 2002, Proceedings of the TAS 2002 Symposium, 6$^{th}$, Nara, Japan (Abstract).

Ren et al., Dynamics of Electro-Wetting Droplet Transport, Nov. 15, 2002, vol. B87, No. 1, pp. 201-206, Sensors and Actuators B (Chemical) (Abstract).

Ren et al., Micro/Nano Liter Droplet Formation and Dispensing by Capacitance Metering and Electrowetting Actuation, 2002, pp. 369-372, Proceedings of the 2002 2$^{nd}$ IEEE Conference on Nanotechnology, Piscataway, NJ (Abstract).

Shvets et al., Spot-On Technology for Low Volume Liquid Handling, 2002, 7/6, pp. 125-129, Journal of the Association for Laboratory Automation (Abstract).

Sommer et al., Parallel Immunoassays on Hydrogel TM Biochips Using Microspot Arrays, 2002, vol. 4626, pp. 49-57, Proceedings of the SPIE—The International Society for Optical Engineering (Abstract).

Aoyama et al., Novel Liquid Injection Method With Wedge-Shaped Microchannel on a PDMS Microchip System for Diagnostic Analysis, 2001, vol. 2, pp. 1232-1235, Transducers '01. Eurosensors XV, 11$^{th}$ International Conference on Solid-State Sensors and Actuators. Digest of Technical Papers (Abstract).

Hicks et al., Modification of an Automated Liquid-Handling System for Reagent-Jet, Nanoliter-Level Dispensing, Apr. 2001, 30(4), pp. 878-885, BioTechniques (Abstract).

Ikemoto et al., A Head-Attachable Device for Injecting Nanoliter Volumes of Drug Solutions Into Brain Sites of Freely Moving Rats, Sep. 30, 2001, 110/1-2, pp. 135-140, Journal of Neuroscience Methods (Abstract).

Koltay et al., Microdispenser Array for Highly Parallel and Accurate Liquid Handling, 2001, vol. 4590, pp. 195-203, Proceedings of SPIE—The International Society for Optical Engineering (Abstract).

Meldrum et al., Automated, Integrated Modules for Fluid Handling, Thermal Cycling and Purification of DNA Samples for High Throughput Sequencing and Analysis, 2001, vol. 2, pp. 1211-1219, 2001 IEEE/ASME International Conference on Advanced Intelligent Mechatronics, Piscataway, NJ (Abstract).

Pearson et al., Microfabrication and Application of Reservoir Pins for Liquid Transfer in Biotechnology, vol. 4407, pp. 281-294, Proceedings of the SPIE—The International Society for Optical Engineering (Abstract).

Pearson et al., Microfluidic Study of the Liquid Transfer Properties of the Liquid Transfer Properties of Reservoir Pins for Use in Microarraying, 2001, vol. 4560, pp. 189-195, Proceedings of SPIE—The International Society for Optical Engineering (Abstract).

Puntambekar et al., A New Fixed-Volume Meteringmicrodispenser Module Based on SPROMS Technology, 2001, vol. 2, pp. 1240-1243, Transducers '01. Eurosensors XV. 11$^{th}$ International Conference on Solid-State Sensors and Actuators. Digest of Technical Papers (Abstract).

Bohm et al., Closed-Loop Controlled Electrochemically Actuated Micro-Dosing System, Dec. 2000, vol. 10, No. 4, pp. 498-504, Journal of Micromechanics and Microengineering (Abstract).

Ducree et al., Production System for Biochips, 2000, vol. 2, pp. 529-533, Proceedings. MICRO. Tec. 2000. VDE World Microtechnologies Congress, Berlin, Germany: VDE Verlag (Abstract).

Katstra et al., Controlling Drug Placement During the Fabrication of Complex Release Oral Forms Using 3DP, 2000, pp. 413-414, Proceedings of the International Symposium on Controlled Release of Bioactive Materials (Abstract).

Katstra et al., Engineering of Complex Oral Delivery Devices Using Three Dimensional Printing, 2000, vol. 28, Supplement 1, pp. S-22, Annals of Biomedical Engineering (Abstract).

Katstra et al., Oral Dosage Forms Fabricated by Three Dimensional Printing, May 3, 2000, 66(1), pp. 1-9, Journal of Controlled Release (Abstract).

Kido et al., Disc-Based Immunoassay Microarrays, May 2000, 411(1-2), pp. 1-11, Analytica Chimica Acta (Abstract).

Meldrum et al., Acapella-1K, A Capillary-Based Submicroliter Automated Fluid Handling System for Genome Analysis, Jan. 2000, 10(1), pp. 95-104, Genome Research (Abstract).

Rowe et al., Multimechanism Oral Dosage Forms Fabricated by Three Dimensional Printing, May 3, 2000, 66(1), 11-7, Journal of Controlled Release (Abstract).

Sastry et al., Recent Technological Advances in Oral Drug Delivery—A Review, Apr. 1, 2000, 3 / 4, pp. 138-145, Pharmaceutical Science and Technology Today (Abstract).

Katstra et al., Pulsatory Oral Drug Delivery Devices Fabricated by Three Dimensional Printing, 1999, 26$^{th}$, pp. 167-168, Proceedings of the International Symposium on Controlled Release of Bioactive Materials (Abstract).

Boillat et al., Controlled Liquid Dosing in Micro-Instruments, 1999, vol. 3877, pp. 20-27, Proceedings of the SPIE—The International Society for Optical Engineering (Abstract).

Meyer et al., Liquid Handling in the Pico- and Nanoliter Range, Apr. 18-21, 1999, pp. 312-319, Microreaction Technology: Industrial Prospects, Proceedings of the International Conference on Microreaction Technology, 3$^{rd}$, Frankfurt (Abstract).

Dilhan et al., Experimentation of an Electrostatically Actuated Monochip Micropump for Drug Delivery, 1999, vol. 3680, pt. 1-2, pp. 887-896, Proceedings of the SPIE—The International Society for Optical Engineering (Abstract).

Meldrum etal., Acapella, A Capillary-Based Submicroliter Automated Sample Preparation System for Genome Analysis, 1999, pp. 39-48 1999 IEEE/ASME International Conference on Advanced Intelligent Mechatronics, Piscataway, NJ, United States: IEEE (Abstract).

Amacker et al., Passive Micro-Flow Regulator for Drug Delivery System, 1998, vol. 1, pp. 591-594, Eurosensors XII. Proceedings of the 12$^{th}$ European Conference on Solid-State Tranducers and the 9$^{th}$ UK Conference on Sensors and their Applications (Abstract).

Backofen et al., Capillary Batch Injection Analysis: A Novel Approach for Analyzing Nanoliter Samples, May 4, 1998, 362/2-3, pp. 213-220, Analytica Chimica Acta (Abstract).

Delamarche et al., Microfluidic Networks for Chemical Patterning of Substrates: Design and Application to Bioassays, Jan. 28, 1998, 120/3, pp. 500-508, Journal of the American Chemical Society (Abstract).

Driscolli et al., Multiprobe NL Components Drug Discovery Assay Miniaturization, Fall 1998, vol. 3, No. 3, pp. 237-239, Journal of Biomolecular Screening (Abstract).

Fernandes, P.B., Technological Advances in High-Throughput Screening, Oct. 1998, 2(5), pp. 597-603, Current Opinion in Chemical Biology (Abstract).

Katstra et al., Oral Dosage Forms by Three Dimensional Printing, 1998, 25$^{th}$, pp. 760-761, Proceedings of the International Symposium on Controlled Release of Bioactive Materials (Abstract).

Lemmo et al., Inkjet Dispensing Technology: Applications in Drug Discovery, Dec. 1998, 9(6), pp. 615-617, Current Opinion in Biotechnology (Abstract).

Stevens et al., Comparison of Automationequiptment in High Throughput Screening, 1998, 3(4), pp. 305-311, Journal of Biomolecular Screening (Abstract).

Fiehn et al., New Technology for the Precision Dosage of Liquids in the Range of Microlitres and Submicrolitres [In German], 1997, 59/9, pp. 814-817, Pharmazeutische (Abstract).

Houston et al., The Chemical-Biological Interface: Developments in Automated and Miniaturised Screening Technology, Dec. 1997, 8(6), pp. 734-740, Current Opinion in Biotechnology (Abstract).

Skardon, J., Applications for Microfluidic Components, 1997, pp. 330-333, WESCON/97. Conference Proceedings, New York, NY, United States:IEEE (Abstract).

Benjamin et al., Solid-Free Form Fabrication of Drug Delivery Devices, vol. 40, No. 1-2, pp. 77-87, Journal of Controlled Release (Abstract).

Fiehn et al., New Technologies for High Precision Dosage, 1996, No. 176, IEE Colloquium (Digest) (Abstract).

Kaartinen, N., Micro Electro Thermo Fluidic (METF) Liquid Microprocessor, 1996, pp. 395-399, Proceedings of the IEEE Micro Electro Mechanical Systems (MEMS), Piscataway, NJ, United States (Abstract).

Stanchfield et al., Precision 96-Channel Dispenser for Microchemical Techniques, 1996, 20(2), pp. 292-296, BioTechniques (Abstract).

Zen'ichi, Y., Utilization of Antibacterial Agent by Thermo-Transfer Printing, 1995, No. 533, pp. 24-26, Sangyo Kikai (Abstract).

Hogan, B., Adhesive Dispenser Provides Plus or Minus 2% Volume Repeatability, Apr. 11, 1994, vol. 49, No. 7, Design News (Boston) (Abstract).

Lammerink et al., Integrated Micro-Liquid Dosing System, 1993, pp. 254-259, Proceedings, IEEE. Micro Electro Mechanical Systems. An Investigation of Micro Structures, Sensors, Actuators, Machines and Systems, New York, NY, United States (Abstract).

Schober et al., Accurate High-Speed Liquid Handling of Very Small Biological Samples, Aug. 1993, 15(2), pp. 324-329, BioTechniques (Abstract).

Bernardini et al., Applications of Piezoelectric Fluid Jetting Devices to Neuroscience Research, Jun. 1991, 38(1), pp. 81-88, Journal of Neuroscience Methods (Abstract).

Martin et al., Automatic Manipulation of Microlitre Volumes of Liquid Reagents, Jan. 1987, vol. 20, No. 1, pp. 22-26, Journal of Physics E (Scientific Instruments) (Abstract).

Kahl et al., General Purpose Multichannel Micro-Dispensing Device, 1976, 48(4), pp. 789-790, Analytical Chemistry (Abstract).

"Online Quality Control with Raman Spectroscopy in Pharmaceutical Tablet Manufacturing," Bonawi-Tan, Winston; Williams, Julie Ann Stuart, Journal of Manufacturing Systems v23n4 pp. 299-308, 2004.

"Photonic analysis creeps toward the production line," Weiss, Stephanie A., Photonics Spectra, v28, n10, p. 98(2), Oct. 1994.

Examination Report dated Feb. 25, 2010 for corresponding Patent Application No. 509/2005 in Pakistan.

International Search Report dated May 2, 2008 from corresponding PCT/US2005/020319.

Russian Office Action for 2006146063 dated Nov. 26, 2007.

Russian Office Action for 2006146063 dated Feb. 16, 2011.

Chilean Office Action for 1383-2005 dated Oct. 5, 2010.

Taiwan Office Action for 94118746 dated Jan. 4, 2011.

Japanese Office Action (English Translation) for 2007-527750 dated Feb. 1, 2011.

Supplementary European Search Report dated Aug. 17, 2011 for European application No. 05760236.

* cited by examiner

APPARATUS AND METHOD FOR PRODUCING OR PROCESSING A PRODUCT OR SAMPLE

RELATED APPLICATIONS

This application is related to, and claims priority in, co-pending U.S. Provisional Application Ser. No. 60/621,992, filed Oct. 25, 2004, the disclosure of which is incorporated herein by reference. This application is also related to, and claims priority in, co-pending U.S. Provisional Application Ser. No. 60/578,245, filed Jun. 9, 2004, the disclosure of which is incorporated herein by reference.

BACKGROUND OF THE INVENTION

1. Field of the Invention

The present invention relates to the manufacture or processing of products or samples. More particularly, the present invention relates to an apparatus and process for manufacturing or processing a product or sample by dispensing.

2. Description of Related Art

Manufacturing processes often require the combination of different materials, such as solder onto a printed circuit board or an active agent onto a pharmaceutical substrate. Various methods have been developed for the combining of such materials. For example, soldering methods have been developed for connecting integrated circuit chips to the printed circuit board. One such method includes applying a small amount of solder to the bottom surface of the chip, aligning the solder with a bond pad on the surface of the printed circuit board, and heating the solder until it reflows. Another such method includes applying solder to bonding pads on the printed circuit board and then bonding electrical components to the printed circuit boards by positioning the components over the solder and by heating and reflowing the solder. In other methods, chips are bonded to a patterned layer of solder created by applying a thin layer of solder paste to a printed circuit board through holes in a stencil, leaving a selected solder pattern on the printed circuit board.

Such methods suffer from drawbacks as to efficiency and quality. Accordingly, there is a need for an apparatus and process for manufacturing products via dispensing that reduces or eliminates these manufacturing and quality control drawbacks of the contemporary devices and techniques.

SUMMARY OF THE INVENTION

It is an object of the present invention to provide a more efficient process and/or apparatus for manufacturing or processing products or samples that comprise a dispensed component.

It is another object of the present invention to provide such a process and/or apparatus that provides real-time process monitoring.

It is yet another object of the present invention to provide such a process and/or apparatus that provides real-time feedback and control of the process and product quality.

It is still another object of the present invention to provide such a process and/or apparatus that provides monitoring of each of the products or samples that are manufactured or processed.

It is yet still another object of the present invention to provide such a process and/or apparatus that minimizes or eliminates off-line quality control inspection and facilitates real-time release of the products.

It is yet a further object of the present invention to provide such a process and/or apparatus that facilitates change over to production of a different product.

These and other objects and advantages of the present invention are provided by a monitoring system for a machine that produces a plurality of products by dispensing droplets of liquid on one or more carrier substrates. The monitoring system comprises an inspection system having a microprocessor, a first camera or video/digital recording device (herein referred to as "camera") in communication with the microprocessor and a trigger operably connected to the first camera. The inspection system determines an amount of the liquid that is being added to each of the carrier substrates. The trigger actuates the first camera to obtain a first image of each of the droplets in-flight. The microprocessor determines the amount of the liquid based upon the first image.

In another aspect, an apparatus for producing a plurality of products is provided. Each of the plurality of products has a carrier substrate and a dispensed liquid thereon. The apparatus comprises a dispensing system for dispensing the dispensed liquid as a droplet onto each of the carrier substrates and a monitoring system comprising an inspection system that determines an amount of the dispensed liquid that is being added to each of the carrier substrates by the dispensing system. The inspection system comprises a microprocessor, a camera or video/digital recording device (herein referred to as "camera") in communication with the microprocessor and a trigger operably connected to the first camera. The trigger actuates the first camera to obtain a first image of the droplet in-flight. The microprocessor determines the amount of the dispensed liquid based upon the first image.

In another aspect, an apparatus for producing a plurality of products that each have a carrier substrate and a dispensed liquid is provided. The apparatus comprises a dispensing system that adds the dispensed liquid to each of the carrier substrates; and a monitoring system that performs real-time monitoring of the dispensing system to determine an amount of the dispensed liquid on each of the carrier substrates.

In another aspect, a monitoring system for a machine that produces a plurality of products is provided where the plurality of products each have a carrier substrate and a dispensed liquid. The monitoring system comprises a confirmation system operably connected to the machine that determines an amount of the dispensed liquid that has been added to each of the carrier substrates by the machine. The confirmation system performs optical profilometry on each of the carrier substrates to determine the amount of the dispensed liquid.

In another aspect, a machine which produces a plurality of products where each has a carrier substrate and a dispensed liquid is provided. The machine comprises a dispensing system for adding the dispensed liquid to each of the carrier substrates and a confirmation system for determining an amount of the dispensed liquid that has been added to each of the carrier substrates. The confirmation system performs optical profilometry on each of the carrier substrates to determine the amount of the dispensed liquid.

In another aspect, a method of monitoring a machine is provided. The machine produces a plurality of products by dispensing a droplet of liquid on a carrier substrate. The method comprises actuating a camera based upon dispensing of the droplet; obtaining a first image of the droplet in-flight; and determining a volume of the droplet based upon the first image.

In another aspect, a method of producing a plurality of products that each have a carrier substrate and a dispensed liquid thereon is provided. The method comprises dispensing the dispensed liquid as a droplet onto each of the carrier substrates; and determining an amount of the dispensed liquid that is being added to each of the carrier substrates by the dispensing system by obtaining a first image of the droplet in-flight and determining the amount of the dispensed liquid based upon the first image.

Each of the carrier substrates can continue to move along the apparatus as the inspection system determines the amount of the dispensed liquid. The monitoring system may further comprise a confirmation system having a probe that performs spectroscopy on the dispensed liquid that has been added to each of the carrier substrates. Each of the carrier substrates can continue to move along the apparatus as the probe performs spectroscopy. The spectroscopy may be taken from the group consisting of near infrared, mid-infrared, ultraviolet/visible, fluorescence, laser-induced fluorescence, Raman, terahertz, and any combinations thereof.

The monitoring system can further comprise a confirmation system having a second camera that obtains a second image of the dispensed liquid on each of the carrier substrates. The confirmation system determines a position of the dispensed liquid for each of the carrier substrates based on the second image. Each of the carrier substrates may continue to move along the apparatus as the second camera obtains the second image.

The apparatus can further comprise a temperature conditioning system that changes the temperature of the dispensed liquid to facilitate its formation on the carrier substrate. The temperature conditioning system may monitor environmental parameters for each of the carrier substrates, wherein the environmental parameters are taken from the group consisting of temperature, air-flow rate, humidity, radiation, product surface temperature, and any combinations thereof.

The apparatus can further comprise a printing system for applying an identification marker to each of the carrier substrates. The printing system may have a third camera for obtaining a third image of the identification marker for inspection. Each of the carrier substrates can continue to move along the apparatus as the third camera obtains the third image.

The apparatus can further comprise a control system for performing real-time control of the dispensing system based on the real-time monitoring. The real-time control may comprise adjusting an amount of dispensing from the dispensing system. The dispensing system may have a nozzle, wherein the real-time control comprises adjusting a position of the nozzle with respect to each of the carrier substrates thereby adjusting the position of the dispensed liquid on each of the carrier substrates. The confirmation system can perform optical profilometry on each of the carrier substrates to determine the amount of the dispensed liquid. Each of the carrier substrates may continue to move along the apparatus as the optical profilometry is performed.

This application is related to the following applications which have been filed contemporaneously herewith and the disclosures of which are hereby incorporated by reference in their entirety: APPARATUS AND METHOD FOR PHARMACEUTICAL PRODUCTION, Ser. No 11/148,919; APPARATUS AND METHOD FOR PRODUCING A PHARMACEUTICAL PRODUCT, Ser. No. 11/148,894; PHARMACEUTICAL PRODUCT, Ser. No. 11/149,100; APPARATUS FOR PRODUCING A PHARMACEUTICAL PRODUCT, Ser. No. 11/148,920; and METHOD FOR PRODUCING A PHARMACEUTICAL PRODUCT, Ser. No. 11/149,022.

Other and further objects, advantages and features of the present invention will be understood by reference to the following:

DETAILED DESCRIPTION OF THE INVENTION

Figure 1:
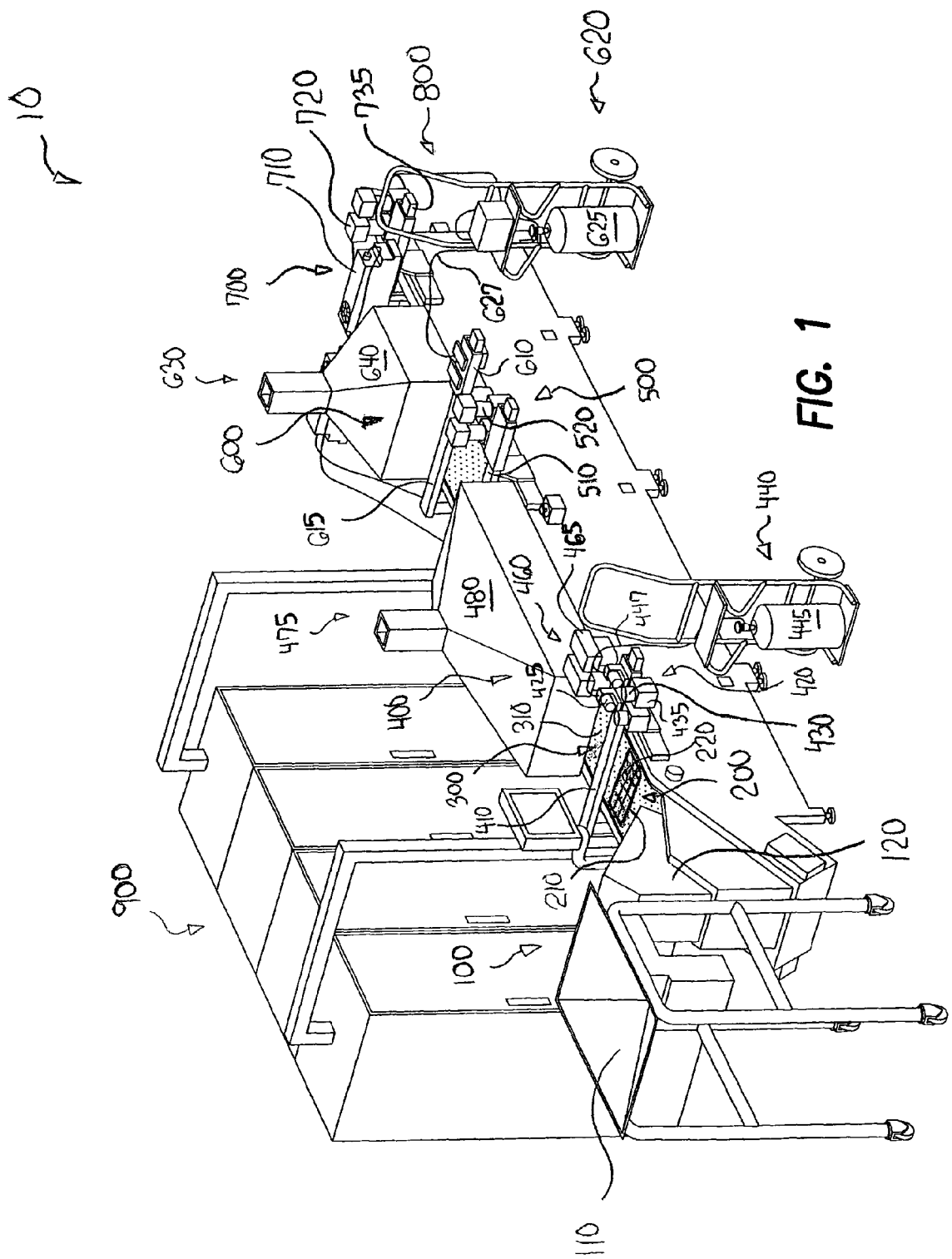
FIG. 1 is a perspective view of a preferred embodiment of a machine of the present invention.
Figure 2:
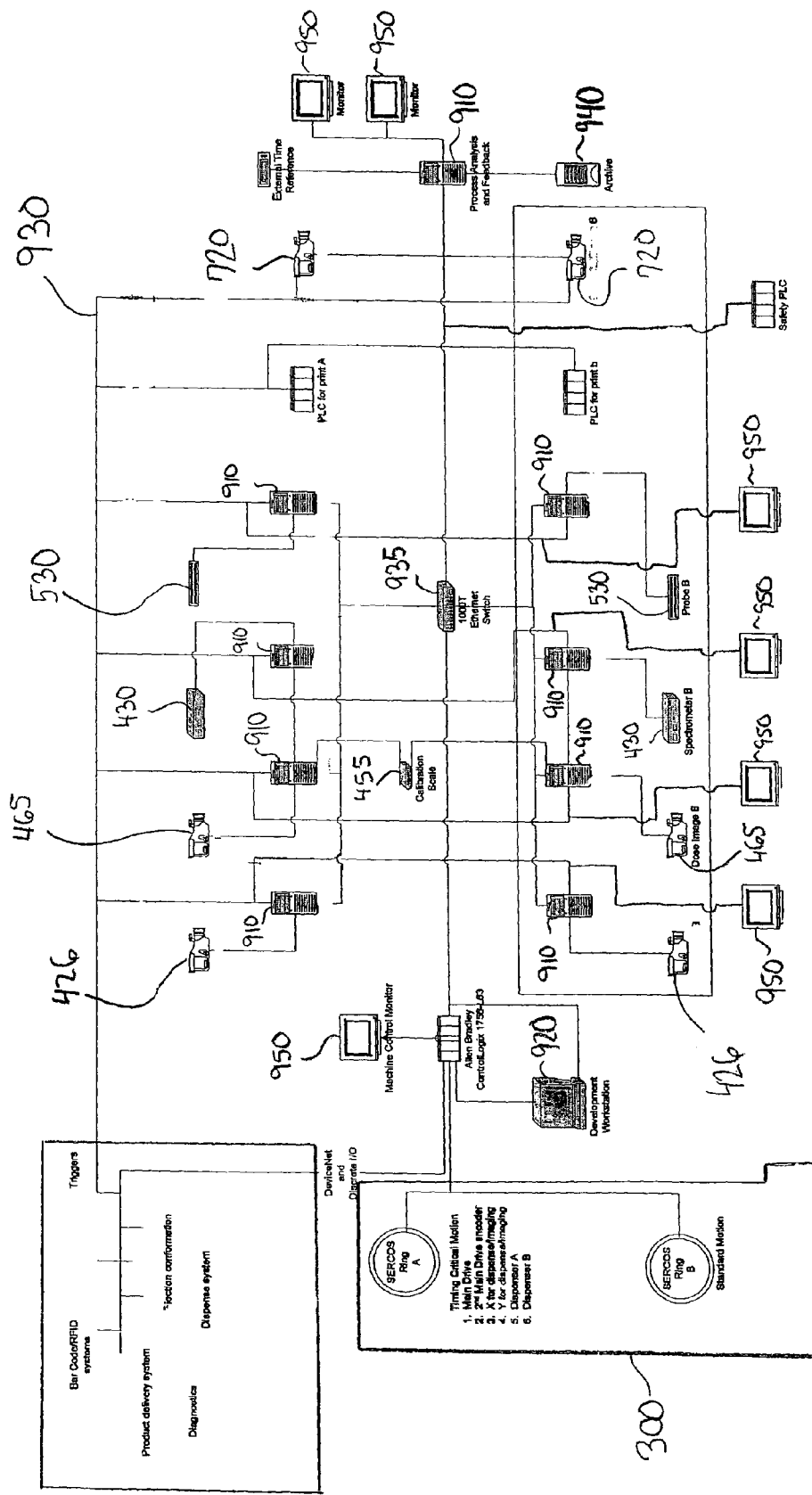
FIG. 2 is a schematic representation of the automation components of the machine of FIG. 1.
Figure 3:
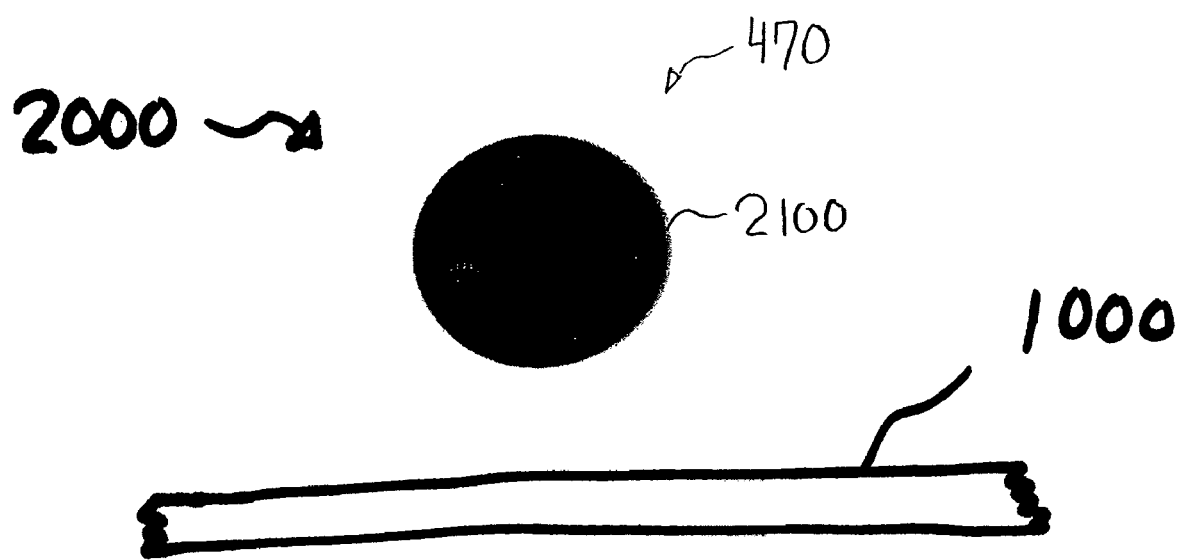
FIG. 3 is a high speed video image of a droplet dispensed by the machine of FIG. 1.

Referring to the drawings, and in particular FIGS. 1 through 3, a preferred embodiment of the apparatus or machine of the present invention is shown and generally referred to by reference numeral 10. The machine 10 has a plurality of components that are operably connected to manufacture a product or process a sample, and preferably a batch of products or samples, as will be described later in greater detail. A batch is a quantity of product, which has been produced or processed during a defined cycle, such as, for example, a fixed number or one or more runs over a fixed time period. The machine 10 has various components arranged along a straight or substantially straight line. However, the present invention contemplates other arrangements and positionings of the various components, such as, for example, in circular or rectangular paths. While the exemplary embodiment describes the manufacture of a product via dispensing, the present invention contemplates other processes being performed by the machines described herein, such as, for example, testing or processing of samples via dispensing.

The arrangement and positioning of the components of machine 10 provide a smaller footprint for space savings, as well as providing a more efficient and ergonomic machine that facilitates operation. Machine 10 can have components stacked on each other or at differing heights to take advantage of vertical space, as well as facilitating operation, such as, for example, enabling the use of gravity in the process performed by the machine.

The machine 10 has a loading system 100, a holding system 200, a conveyor system 300, a dispensing system 400, a coating system 600, a printing system 700, a product acception-rejection system 800, and a control system 900. Each of these systems 100 through 900 are operably connected to each other to efficiently and ergonomically provide products that are ready for packaging, and which have each undergone real-time monitoring, and preferably real-time feedback and adjustment or control.

The machine 10 delivers the product, which is a combination of a substrate 1000 and a liquid 2000. As will be described later in greater detail, the liquid 2000 is dispensed by dispensing system 400 in the form of a droplet 2100 (shown in FIG. 3) that is dispensed onto the substrate 1000. It should be understood that the liquid 2000 can have a variety of properties, such as, for example, low-viscosity, high-viscosity, such that the term liquid is not intended to be limiting. The liquid 2000 can be anything that is dispensable onto the substrate 1000, such as, for example, solder onto an IC chip or a therapeutic active agent onto a carrier tablet. One of ordinary skill in the art could utilize the present invention for processing a variety of substrates 1000 with a variety of liquids 2000. Additionally, the dispensing of liquid 2000 onto substrate 1000 is not limited to droplets 2100, but can also include other flow patterns, such as, for example, a partial or continuous stream. It should be further understood that the present disclosure contemplates the substrate 1000 being a variety of substances upon which the liquid 2000 can be dispensed and having a variety of properties. Such a substance for substrate 1000 may also include another liquid.

The droplet 2100 is dispensed onto the outer surface or substantially along the outer surface of the substrate 1000, such as, for example, solder that is heated and then dispensed onto the substrate. The substrate 1000, the liquid 2000 and the resulting product undergo real-time monitoring, feedback and adjustment, which improve quality control.

In the preferred embodiment shown in FIG. 1, loading system 100 has a loading container or hopper 110 in communication with a loading chute 120. Hopper 110 is preferably movable so that one or more substrates 1000 can be loaded into the hopper and then the hopper can be moved into communication with the loading chute 120. Loading chute 120 is in communication with holding system 200 and conveyor system 300 so that the substrates 1000 can be moved from the hopper 110 into the holding system 200 for movement along and through machine 10 by way of conveyor system 300.

The hopper 110 and loading chute 120 can use various devices and methods, such as, for example, powered wheels or wedges, powered belts, or gravity, to move each of the substrates 1000 into their designated positions in holding system 200. In machine 10, a portion of loading system 100 is preferably disposed above a portion of conveyor system 300 to take advantage of gravity, in combination with a mechanical loading device.

In the preferred embodiment, holding system 200 has a plurality of holding members or trays 210 with substrate positions 220 having a size and shape that allows for holding of each of the substrates 1000. Preferably, each of the holding trays 210 is rectangular, and the substrate positions 220 are arranged in an array of equi-distantly spaced rows and columns. As will be explained later, this array facilitates operation of the dispensing system 400 in adding the droplets 2100 to the substrates 1000. However, the present invention contemplates the use of other structures and methods for securing each of the substrates 1000 and the resulting products as they travel along machine 10.

One of ordinary skill in the art can vary the sizes, capacities and shapes of the holding trays 210 and the substrate positions 220 to accommodate different shapes and/or sizes of substrates 1000 and to increase efficiency. Additionally, the holding trays 210 may simply be a mechanism for temporarily connecting the substrate 1000 with the conveyor system 300 so that the substrate travels along the machine 10, such as, for example, a large substrate receiving multiple dispensings thereon.

Holding system 200 tracks individual substrates 1000 by their designation in each of the substrate positions 220. This allows machine 10 to perform various real-time monitoring, feedback and adjustment activities upon each of the substrates 1000, droplets 2100 and products, and also to make determinations as to whether each of the substrates, droplets or resulting products have met the quality control standards that are designated for a particular product. The tracking of each of the substrates 1000, droplets 2100 and/or products throughout the process carried out by machine 10, allows for acceptance or rejection during the process. The present invention also contemplates tracking of unacceptable substrates 1000 for removal by acception-rejection system 800 based on the real-time monitoring.

Various tracking or identification methods can be used by holding system 200 for each of the substrates 1000. In the preferred embodiment of machine 10, holding trays 210 have a bar code 230 that can be scanned to provide identification and information to control system 900, and which can also be used to track and monitor the individual substrates 1000, droplets 2100 and/or products throughout the process. As will be discussed later in greater detail, the data compiled throughout the process is stored by control system 900. The data is based upon the individual substrates 1000, droplets 2100 and/or products, as opposed to contemporary quality control methods that use batch-sampling.

In the embodiment of machine 10, holding system 200 positions each of the substrates 1000 so that dispensing system 400 can add the droplet 2100 to the outer surface of the substrate, which is facing away from the holding tray 210. The present invention contemplates the dispensing system 400 also adding the droplet 2100 to the opposing outer surface of the substrate 1000. This would allow for a greater capacity of liquid 2000 being carried by the substrate 1000 (on both of its outer surfaces).

Dispensing onto both sides of the substrate 1000 would also provide the ability for different liquids 2000, to be dispensed upon a single substrate, such as, for example, where the different liquids are incompatible and cannot be mixed together in liquid form or where the different liquids cannot be layered on top of each other. The present invention contemplates dispensing system 400 adding one or more different liquids 2000 to substrates 1000 through layering, through depositing on opposing outer surfaces and/or both. The present invention also contemplates dispensing system 400 adding a plurality of different liquids 2000 to substrates 1000, where the liquids are simultaneously on one or both of the outer surfaces of the substrate.

Machine 10 can also be used to re-process the substrates 1000 any number of times through the dispensing system 400 in order to add each of the different liquids 2000. Machine 10 may have additional dispensing systems 400 in series that will add each of the different liquids 2000 to the substrates 1000.

Holding system 200 can alternatively provide for dispensing the liquid 2000 (or different liquids) on both sides of the substrates 1000 by providing dispensing system 400 with access to both sides of the substrate. Examples of such alternative methods of dispensing include, but are not limited to, inverting holding tray 210 so that each of the substrates 1000 are transferred into a second holding tray 210 so that the opposing outer surfaces are now facing away from the second holding tray or using a holding tray that holds each of the substrates around their perimeters or outer circumferences so that both outer surfaces are simultaneously accessible.

The flipping or inverting of each of the carrier substrates 1000 or their holding tray 210 can be done near the end of the process so that the opposing outer surface is re-processed by the same components or a second set of components could be added to machine 10 to continue the process with respect to the opposing outer surface. Additionally, the inverting of each of the substrates 1000 or their holding tray 210, can be done by holding system 200 to allow for other operations or processes to be performed on the opposing outer surface, such as, for example, coating or printing on both sides of the products.

Conveyor system 300 provides for movement of holding trays 210 along machine 10 and through the various stages or systems of the machine. In the preferred embodiment of machine 10, conveyor system 300 provides for movement of holding trays 210 along a substantially horizontal path. However, the present invention contemplates movement of the holding trays 210 in other directions, such as, for example, in a vertical path, where spacial economy, the use of gravity or other reasons suggest or dictate such a direction of movement.

Conveyor system 300 has a drive conveyor 310. Drive conveyor 310 is controlled by control system 900, shown in FIG. 1, and is preferably variable speed. Holding trays 210 are preferably removably connected to drive conveyor 310. Holding trays 210 are securely connected to the drive conveyor 310 so that each of the substrate positions 220 remains constant with respect to the drive conveyor in order to provide accuracy in dispensing and monitoring of the substrates 1000, droplets 2100 and products. In the preferred embodiment of machine 10, drive conveyor 310 is a circulating conveyor belt that traverses the length of machine 10 and, more preferably, is a serial real-time communications system drive unit. However, the present invention contemplates other types and methods of moving the holding trays 210, such as, for example, parallel drive chains, tracks, belts or wheels to which the holding trays can be removably connected.

The present invention also contemplates the use of a number or series of holding trays 210 that are pivotally secured to each other to form a belt-like structure or tray belt, which can be operably connected to the drive conveyor 310. Machine 10 can have a plurality of tray belts with different sizes and/or shapes of substrate positions 220 to accommodate different sizes and/or shapes of substrates 1000. The tray belt is a length or line of holding trays 210 that is connectable at opposing ends to form a loop. When the holding trays 210 are to be replaced for different products, the tray belt is fed along the drive conveyor 310 and then secured at its opposing ends to form the belt along the machine 10. To expedite the connection of the second tray belt to drive conveyor 310, the second tray belt can preferably be connected to the end of the first tray belt that is being removed, as that first tray belt is driven along and off of the drive conveyor.

The present invention also contemplates the use of any number of drive conveyors 310. For example, different systems of machine 10 can have independent drive conveyors 310 that allow for independent control of the speed of the drive conveyors, such as, for example, to more rapidly remove the products from the end of the process. In such an alternative embodiment, control system 900 would preferably control the various independent drive conveyors 310, and be able to coordinate their movement.

In the preferred embodiment, dispensing system 400 provides for the addition of the liquid 2000 to each of the substrates 1000, and provides for real-time monitoring, feedback and adjustment. To dispense the liquid 2000, dispensing system 400 has a gantry 410 that laterally spans above and across drive conveyor 310, and is longitudinally movable with respect to the drive conveyor. The movement of gantry 410, including speed and position, is controlled by control system 900.

The gantry 410 has a dispensing module 420 movably connected thereto. The dispensing module 420 is movable along the longitudinal axis of the gantry 410, which laterally traverses across the drive conveyor 310. The movement of the dispensing module 420, including speed and position, is also controlled by the control system 900.

Based upon the movement of the gantry 410, and its own movement with respect to the gantry, the dispensing module 420 is capable of movement along X and Y axes with respect to the drive conveyor 310 and the holding trays 210. Additionally, the present invention contemplates movement of the gantry 410, the dispensing module 420, and/or both, along a Z-axis with respect to the drive conveyor 310 and the holding trays 210. The movement of the dispensing module 420 allows it to accurately dispense the droplet 2100 on each of the substrates 1000 that are in the array of substrate positions 220 on holding tray 210. Control system 900 can also adjust the movement of the dispensing module 420 and the gantry 410 to accommodate different sizes and shapes of holding trays 210, as well as different arrays of substrate positions 220 on the holding trays.

Figure 2A:
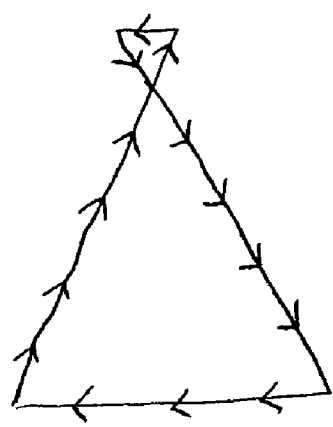
FIG. 2a is a representation of a path of continuous movement of the dispensing module of the machine of FIG. 1.
Figure 2B:
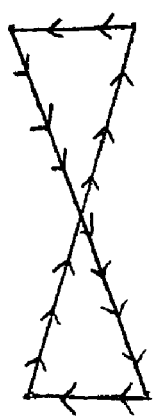
FIG. 2b is a representation of another path of continuous movement of the dispensing module of the machine of FIG. 1.
Figure 2C:
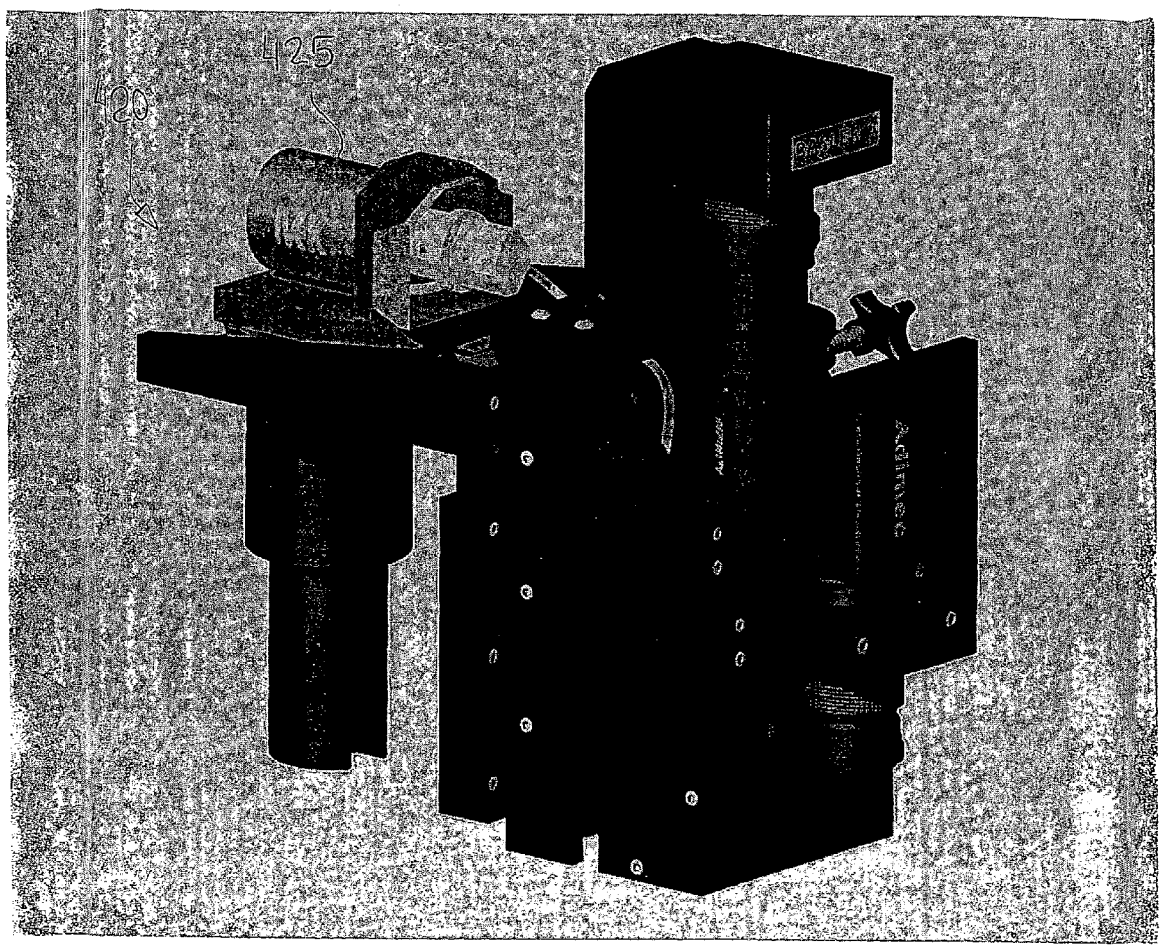
FIG. 2c is a perspective view of a dispenser assembly of the machine of FIG. 1.
Figure 2D:
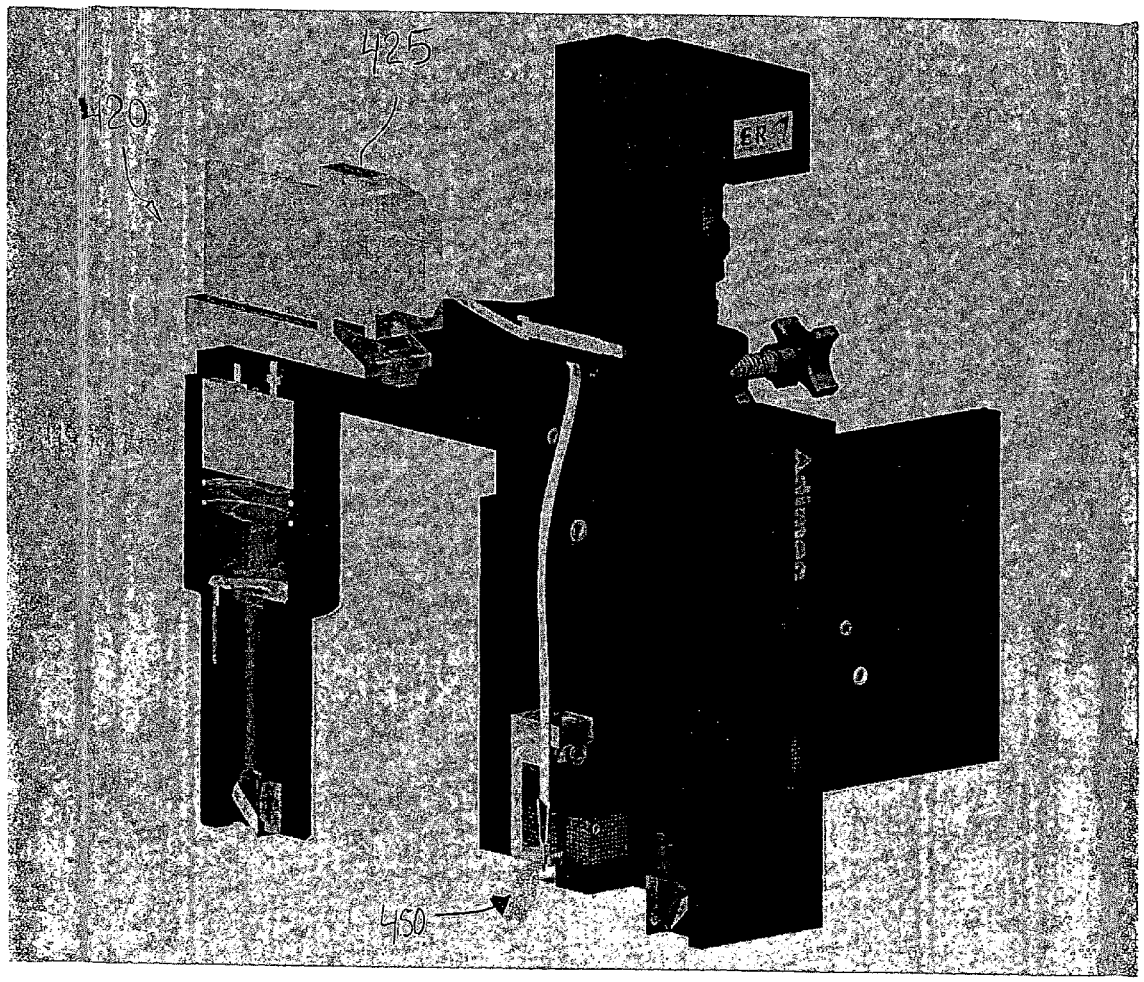
FIG. 2d is a perspective cross-sectional view of the dispenser assembly of FIG. 2c.

The use of the gantry 410 to move the dispensing module 420 along X and Y axes (and the Z axis if desired), provides for smooth movement and accurate alignment of the dispensing module with each of the substrates 1000. This is especially significant in the preferred embodiment of machine 10 where the drive conveyor 310 continues to move the holding tray 210 through the dispensing system 400 as the droplets 2100 are being dispensed. The continuous movement of each of the substrates 1000 along machine 10 as the dispensing step is occurring speeds up the manufacturing process. Additionally, smooth continuous movement of the holding tray 210 and the substrates 1000 thereon, as opposed to dispensing onto the substrates via indexing or discontinuous movement, provides for less wear and tear on the machine 10 and its components, particularly the drive conveyor 310. Dispensing module 420 preferably moves in an X-like path to accurately dispense on each of the substrates 1000. The size and shape of the X-like path depends upon the dispensing speed and the spacing of substrate positions 220, as shown in FIGS. 2a and 2b. It should be further understood by one of ordinary skill in the art that the dispensing module 420 can be moved along alternative paths that preferably allow for continuous movement of the substrates 1000 during dispensing.

The accuracy of the alignment of the dispensing module 420 with each of the substrates 1000, and the efficiency of the movement of the module, is facilitated by the use of the rectangular array of substrate positions 220 along holding tray 210 and the control of the movement of the module and gantry 410 in a rectangular coordinate system. However, the present invention contemplates the use of other structures and methods that could also be used to move the dispensing module 420 with respect to each of the substrates 1000, as the drive conveyor 310 continues to move through the dispensing system 400, such as, for example, a multiple axis robotic arm and/or along different coordinate systems.

In the preferred embodiment of machine 10, the dispensing system 400 has a pair of dispensing modules 420 connected to gantry 410. The use of more than one dispensing module 420 provides for increased speed and efficiency in dispensing of the liquid 2000. Additionally, the use of more than one dispensing module 420 would allow the dispensing system 400 to add different liquids 2000 to a substrate 1000 without cleaning or replacing the module, such as, for example, in layering or on opposing outer surfaces through re-processing the substrate back through the dispensing system.

Dispensing module 420 dispenses a desired amount of liquid 2000 onto the substrate 1000. In the preferred embodiment of machine 10, the dispensing module 420 has a pump 425, a flow cell or meter 430, and a dispensing head 435. The present invention contemplates a single dispensing module 420 that has duplicate components, such as, for example, a pump 425 and a flow cell 430 that are in fluid communication with a pair of dispensing heads 435, and/or other combinations or numbers of components for any number of dispensing modules.

The pump 425 is connected to a liquid source 440. In the preferred embodiment of the machine 10, the liquid source 440 is a movable container 445 that is connected to the pump 425 via removably connectable conduit 447, so that the liquid 2000 can be quickly and efficiently replaced. The liquid source 440 can have a heater (not shown) to facilitate flow of the liquid 2000 from the container 445 to the pump 425, such as, for example, where the liquid is a solder or other type of material that is generally in a solid state at room temperature.

The present invention contemplates the use of a liquid source 440 with replaceable cartridges, containers or canisters (not shown) that can be easily inserted in, or connected to, the liquid source. For lower amounts of the liquid 2000 to be dispensed, having a liquid source 440 that is held in replaceable cartridges, containers or canisters is especially useful for facilitating operation of machine 10.

The pump 425 is preferably a metered, positive displacement pump (shown in FIGS. 2c through 2f), which causes the dispensing head 435 to dispense a single droplet 2100. The metered, positive displacement pump 425 is controlled by the control system 900, and facilitates the accuracy and control of dispensing a single droplet 2100 of the desired size so that the proper amount of liquid 2000 is added to the substrate 1000. However, the present invention contemplates the use of other types of pumps, such as, for example, a time-pressure pump or reciprocating piston pump connected to a dispensing module that can provide the same degree of accuracy and speed in adding the liquid 2000 to the substrate 1000.

Figure 2E:
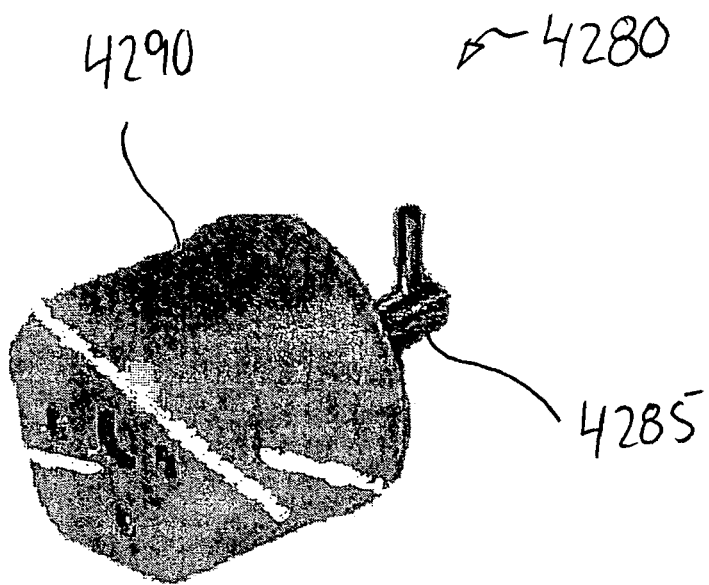
FIG. 2e is a perspective view of the pump module of the dispenser assembly of FIG. 2c.
Figure 2F:
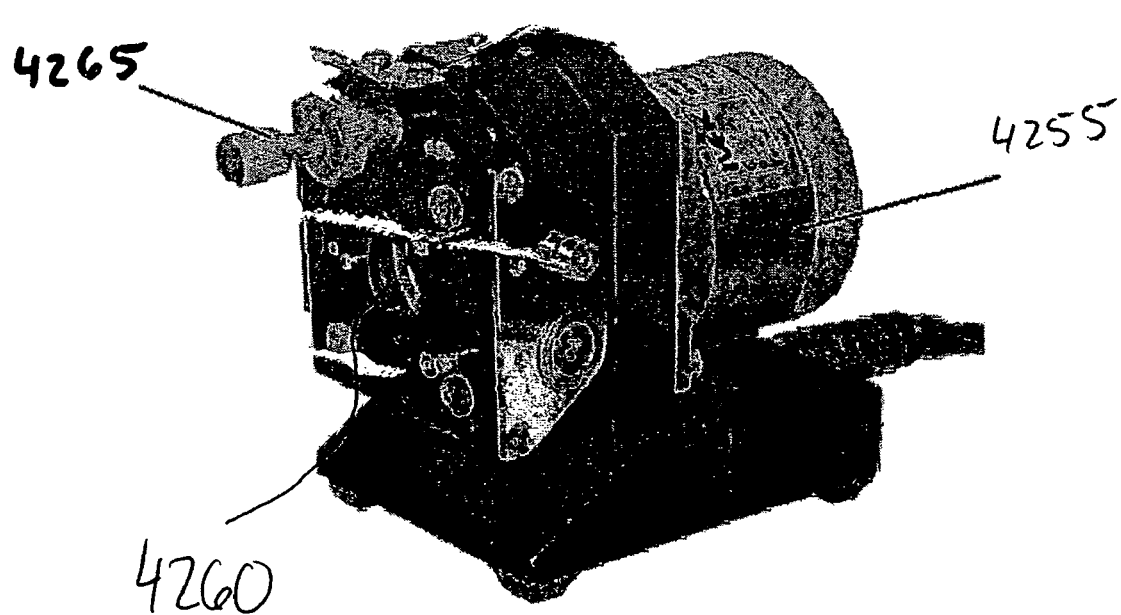
FIG. 2f is a perspective view of the motor module of the dispenser assembly of FIG. 2c.

Pump 425 has a motor module 4250 and a piston module 4280, as shown in FIGS. 2e and 2f. The motor module 4250 has a motor 4255, a connection port 4260 and an adjustment mechanism 4265. The piston module 4280 has a piston assembly 4285 and a cylinder 4290. When the piston module 4260 is operably connected to the motor module 4250 through connection port 4260, the piston on piston assembly 4285 is driven which imparts both reciprocating and rotary motion to the piston. The magnitude of the piston stroke is manually adjustable by the adjustment mechanism 4265. The present invention contemplates automatic adjustment through use of the real time monitoring, feedback and control as described herein.

Pump 425, as controlled by the control system 900, can skip select substrate positions 220, where the substrates 1000 contained therein have been designated as rejected. Machine 10 provides for inspection of the substrates 1000 before they undergo the dispensing process described above. In the preferred embodiment, the substrate inspection is performed by a camera 426 and gantry assembly (not shown), which provide images of each of the substrates 1000 for inspection by control system 900.

Alternative inspection devices and methods can be used which determine the condition of the substrate, as well as ensure that it is properly positioned in substrate position 220. Selective dispensing by pump 425 improves efficiency by not wasting any liquid 2000 on any substrates 1000 that have already been deemed to not meet the required tolerances of the products or are not properly positioned for receiving the droplet 2100.

The pump 425 is connected to the flow cell 430. The flow cell 430 determines the amount of liquid 2000 contained in container 445 that is going to be dispensed through the dispensing head 435, which will be used in the real-time monitoring of the droplets 2100.

The dispensing head 435 has a dispensing nozzle 450 (shown in FIG. 2d) through which the pressurized, metered amount of liquid 2000 is dispensed, and forms the droplet 2100. The droplet 2100 dispenses onto the outer surface of the substrate 1000.

Nozzle 450 provides for exact amounts of liquid 2000 being dispensed. The liquid 2000 is preferably dispensed by a very precise, positive displacement, piston pump 425 that pumps the liquid through tubing to the nozzle 450. The proper selection of liquid composition, viscosity, the materials of construction and orifice size of the nozzle 450 are significant and/or critical parameters to the reproducibility of droplets formed.

Nozzle 450 can also be made from a hydrophobic material and/or have a hydrophobic coating to facilitate formation and dispensing of droplet 2100 by compensating for liquid vehicle composition/formulation and surface tension.

Figure 2G:
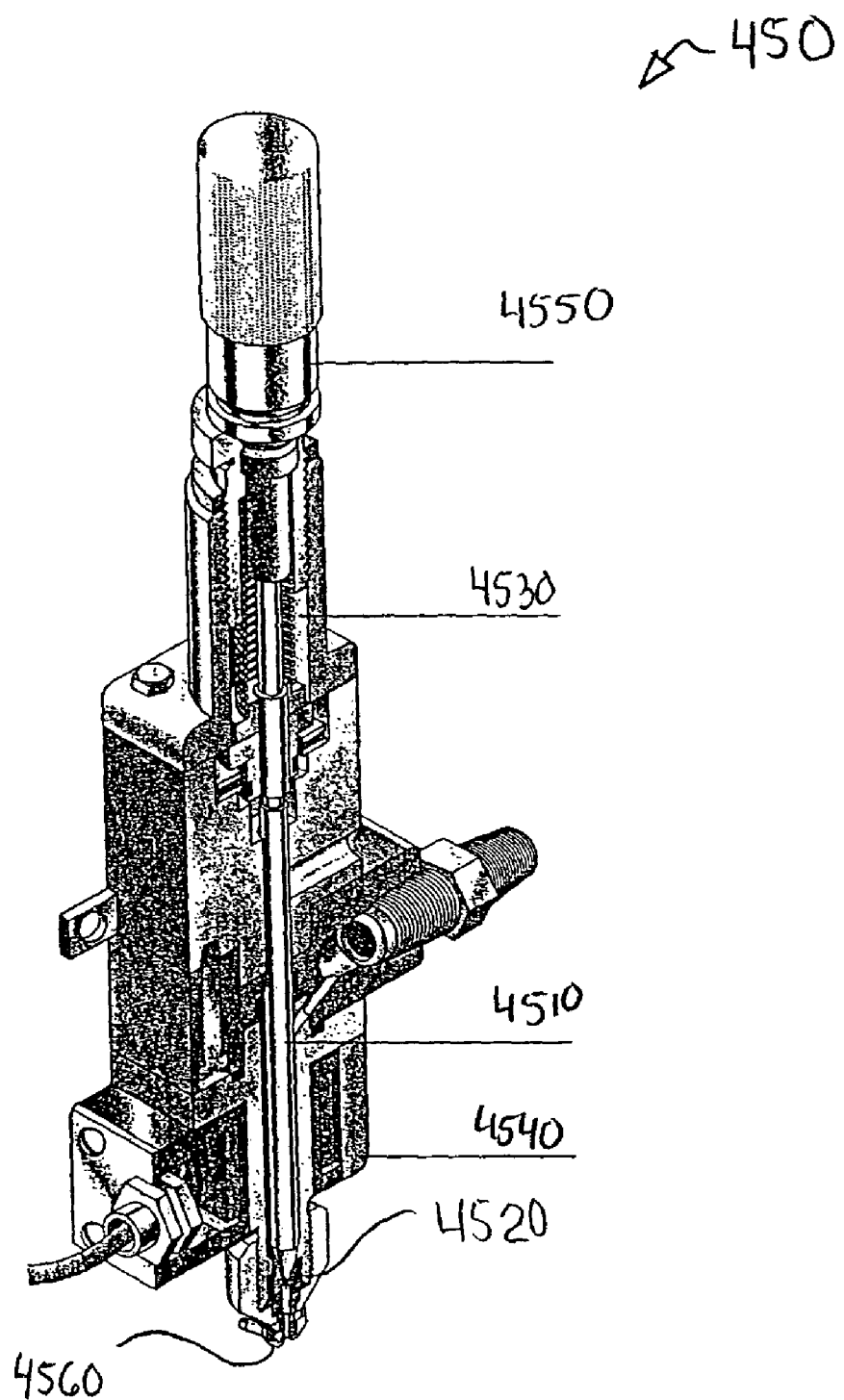
FIG. 2g is a perspective cross-sectional view of another embodiment of a nozzle of the machine of FIG. 1.

In an alternative embodiment shown in FIG. 2g, nozzle 450 has an internal plunger 4510 that is retracted to allow the exact amount of liquid 2000 to enter the dispensing chamber 4520 under pressure of pump 425. Preferably, plunger 4510 is spring-loaded by a spring 4530, or other biasing device, and can be retracted by air pressure, such as, for example, by a solenoid driven pressure source. The liquid 2000 is dispensed as a result of the retraction of the plunger 4510. Under automatic control, the time that the plunger 4510 is in the open position, the pressure maintained on the reservoir of liquid and the vehicle composition are significant and/or critical parameters to the reproducibility of the droplets formed.

Chamber 4520 is preferably selectively sealed so that the chamber and liquid 2000 contained therein remain under pressure. A heater 4540 may be utilized to facilitate the ejection process. Nozzle 450 may have a micro-adjuster 4550 or other adjustment mechanism, manual or automatic (such as being controlled by control system 900 with real-time monitoring, feedback and control), that provides for adjustment of the amount of liquid 2000 that is allowed to exit the dispensing chamber 4520. Nozzle 4560 may be a co-axial air exhaust 4560 that further facilitates dispensing of liquid 2000.

The dispensing system 400 uses a pump and nozzle assembly to form and dispense the droplet 2100. This is advantageous due to the accuracy of the components as described above, and the ability to perform real-time monitoring of their activities. Also, the dispensing system 400, through use of nozzle 450, can preferably provide a spherical or substantially spherical droplet 2100, which reduces or prevents splashing and overspray. Additives can be provided to liquid 2000 to facilitate dispensing where appropriate.

The dispensing system 400, and the use of a liquid 2000 and droplet 2100 that are dispensed onto the substrate 1000, is advantageous over contemporary systems and processes in that the production facilities or sites where the machine 10 is located can centrally process the liquid. This reduces the steps of the production, such as eliminating off-site production and delivery, which decreases production time and saves on costs. Where harmful compounds are being used in the liquid 2000, this is especially advantageous in reducing the handling of the compounds by the workers.

Figure 2H:
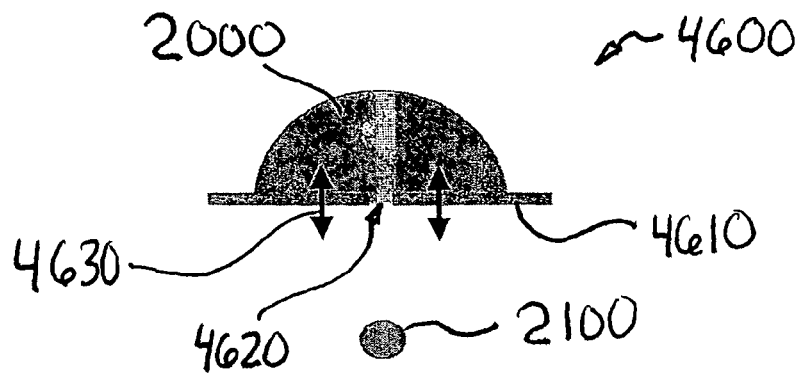
FIG. 2h is a schematic representation of another embodiment of a dispensing assembly of the machine of FIG. 1.
Figure 2I:
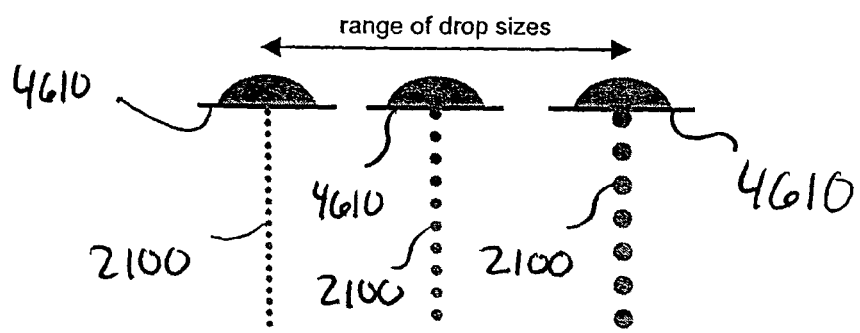
FIG. 2i shows the range of droplets that can be dispensed from the assembly of FIG. 2h.
Figure 2J:
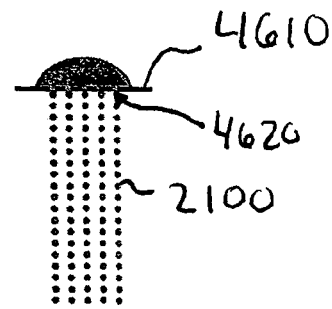
FIG. 2j shows the dispensing assembly of FIG. 2h with multiple nozzles or apertures.

Dispensing system 400 can alternatively have a nozzle-plate assembly 4600 (a portion of which is schematically represented in FIGS. 2h through 2j) to form and dispense the droplet 2100. The assembly 4600 has a plate 4610 with an aperture or nozzle opening 4620 therethrough. The plate 4610 is capable of movement with respect to the supply of liquid 2000, as indicated by arrows 4630. Such movement includes, but is not limited to, vibration of the plate 4610 in order to actuate the dispensing. The liquid 2000 is dispensed through nozzle opening 4620 when the plate 4610 is selectively moved towards the supply of the liquid.

As shown in FIG. 2i, the size of nozzle opening 4620 can be adjusted or changed to provide for a range of different sizes or volumes for droplet 2100. The ability to accurately size very small openings in plate 4610 and the dispensing dynamics of the assembly 4600 allow for dispensing of very small amounts of liquid 2000. As shown in FIG. 2j, a number of nozzle openings 4620 can also be used in the plate 4610 so that array dispensing can be done.

Nozzle-plate assembly 4600 is advantageous due to its minimization of components so that there are fewer materials in contact with the liquid 2000. The dispensing operation of the assembly 4600 is reliable since there are no narrow channels and the design is insensitive to air entrapment. Dispensing through the movement of plate 4610 makes the assembly 4600 easy to load and easy to clean. Dead volume for the supply of liquid 2000 is minimized or eliminated due to the planar or substantially planar shape of plate 4610.

The present invention further contemplates the use of other structures and methods of dispensing the liquid 2000 onto the substrate 1000, such as, for example, by a pad-printing device where the liquid 2000 is loaded into the ink cartridge.

Dispensing system 400 has a dispensing inspection system 460 that provides real-time monitoring of each droplet 2100 that is to be added to the substrates 1000. In the preferred embodiment of the machine 10, dispensing inspection system 460 uses high-speed imaging of the droplet 2100 to determine the volume of the droplet. Dispensing inspection system 460 has a high-speed camera 465, preferably a digital camera, that is connected to gantry 410 and which is able to take a high-speed image 470 (shown in FIG. 3) of each droplet 2100. In the preferred embodiment of machine 10, two high-speed, preferably digital, cameras 465 are used, which correspond to each of the two dispensing modules 420.

The image 470 of the droplet 2100 is preferably taken in-flight after the droplet has left the nozzle 450 but before it makes contact with substrate 1000. The machine 10 uses a laser detector to trigger the camera 465 to obtain the image 470 due to the high speed of the droplet 2100 (shown generally in FIG. 2d). However, the present invention contemplates the use of other triggering devices and methods for triggering camera 465 and obtaining image 470.

Image 470 is used by the control system 900 to calculate a volume of each of the droplets 2100. The calculated volume of the droplet 2100 is used to determine the amount of liquid 2000 that is being dispensed onto the substrate 1000. Any amount of liquid 2000 that does not meet tolerances will be marked with an error code by control system 900 so that the substrate 1000 having that particular droplet 2100 can be rejected.

Where larger amounts of liquid 2000 are required in a product, dispensing module 420 may dispense a number of droplets 2100 or a stream of liquid. Dispensing inspection system 460 still has the ability to capture the image 470 of the stream of liquid 2000, and the volume calculations can be made therefrom.

Dispensing system 400 has a temperature conditioning system 475 that performs cooling/heating/drying of the droplet 2100 on the substrate 1000 depending upon the particular liquid 2000 that has been dispensed, such as, for example, solder may be subjected to cooling to transform it to its solid state while a therapeutic active agent may be subjected to drying to form a film on a carrier tablet. In the preferred embodiment of the machine 10, temperature conditioning system 475 has a temperature conditioner 480 and temperature conditioner sensors or monitors 482 (not shown in detail). The temperature conditioner 480 provides a temperature change to the droplet 2100 and substrate 1000, such as, for example, heating, cooling and/or air flow. Various components can be used for temperature conditioner 480, such as, for example, an oven, refrigeration/cooling device and/or fan. The temperature conditioner sensors 482 monitor the conditions or environmental parameters of each of the dispensed droplets 2100 and substrates 1000 to ensure that the products meet the required tolerances.

Conditions, such as, for example, temperature, air-flow and humidity are monitored by the temperature conditioner sensors 482, and a number of such sensors are used to account for any variance along the temperature conditioner 480. The data gathered by the sensors is provided to control system 900 for evaluation of the quality of the substrates 1000 and droplets 2100 in each of the holding trays 220.

In the preferred embodiment, the drying conditions are monitored for the entire holding tray 220, and error codes can be assigned to the individual substrates 1000 and droplets 2100 contained therein, based upon a holding tray being affected by a condition of the temperature conditioner 480 that does not meet the required tolerances. Alternatively, portions of trays can be monitored for drying conditions by placing more sensors 482 in the temperature conditioner 480 in strategic positions. Additionally, the present invention contemplates the monitoring of other conditions or criteria related to the temperature conditioning process, such as, for example, conditions that may be more significant to particular products.

The present invention also contemplates temperature conditioner 480 being an infrared (IR) temperature conditioner and/or having a combination of IR, convection, conduction and/or microwave heating. Temperature conditioning system 475 can include sensors to detect conditions, such as, for example, the surface temperature of the substrates 1000, or IR radiation. Temperature conditioning system 475 may also include a sensor for turning on the temperature conditioner, such as, for example, a photo-cell triggered by holding trays 210 entering the temperature conditioner 480. Additionally, temperature conditioner 480 can be utilized for heating of the substrate 1000 to cause reflow, such as for dispensed solder.

Dispensing system 400 has a dispensing confirmation system 500 that provides real-time monitoring, feedback and adjustment for the liquid 2000 that has been added to the substrate 1000. In particular, the dispensing confirmation system 500 monitors the positioning of the liquid 2000 on the substrate 1000 and the amount of the liquid contained thereon. Additionally, the dispensing confirmation system 500 can monitor for other substances, such as, for example, identifying contaminants present on the substrate 1000, as well as the amount of such other substances.

The data obtained by the dispensing confirmation system 500 is provided to the control system 900. The control system 900 will assign error codes to individual substrates 1000 and their liquids 2000 that do not meet the required tolerances of the product.

In the preferred embodiment of the machine 10, dispensing confirmation system 500 has a gantry 510 (similar to gantry 410 described above) with a pair of charge coupled device (CCD) cameras 520 that obtain images 525 of each of the substrates 1000. The images 525 are provided to control system 900 for a determination of the position of the liquid 2000 with respect to the substrate 1000. For example, the position of solder on an IC chip can be analyzed via image 525 to determine the strength of the bond, as well as short circuits or the potential risk of short circuits.

Dispensing confirmation system 500 can also have a probe 530 (shown in FIG. 2) that is used for determining the amount, type and/or distribution of the liquid 2000 on the substrate 1000. In the preferred embodiment of machine 10, the probe 530 uses chemical imaging to determine the amount of the liquid 2000 present on the substrate 1000. The present invention contemplates dispensing confirmation system 500 providing other analysis for the liquid 2000, such as, for example, mechanical stress, crystallinity, crystal orientation, composition, crystal phase, and/or doping.

Probe 530 has components that carry out chemical imaging on each of the substrates 1000 in holding tray 210, such as, for example, fiber optics, focal plane array (FPA) detectors, and/or charge coupled device (CCD) detectors. Additionally, liquid crystal tunable filters can be used as wavelength selectors for the chemical imaging. The chemical imaging provides good penetration into the liquid 2000 and upper surface of the substrate 1000 for an accurate measurement of the quantity of the liquid.

In the preferred embodiment of machine 10, probe 530 uses a focal plane array detector to obtain a signal from every point in the sample area. The sample area preferably includes the entire holding tray 210 so that all of the substrates 1000 are being simultaneously measured, which further improves the efficiency of the process. The focal plane detector is able to obtain simultaneous spectral information at every frequency for the sample area. Probe 530 can rapidly and non-destructively measure the liquid 2000 for various characteristics including, but not limited to, amount, formulation and/or distribution, as well as monitor or detect other substances contained in or on the substrate 1000.

The present invention contemplates the use of various methods and devices for determining the presence, type, distribution, amount or other characteristics of a particular liquid 2000 on the substrate 1000, such as, for example, spectroscopy and/or chemical imaging utilizing Raman and UV reflectance, and various other types of imaging, chemical imaging and/or spectroscopy, such as, for example, UV/visible absorption, fluorescence, laser-induced fluorescence, luminescence, photoluminescence, terahertz, NIR and mid-IR. The present invention contemplates the use of various devices or components that facilitate the use of spectroscopy and/or chemical imaging for analysis of the products, such as, for example, lasers (e.g., pulse lasers), beam splitters, water-vapor free environments (e.g., nitrogen shrouds), optical delays (e.g., variable optical delays), antennas and/or semiconductors. The present invention contemplates the use of room temperature solid state detectors and/or pulsed time-gated techniques and components. The present invention contemplates the use of techniques for analysis of the products that are non-ionizing, non-invasive, non-destructive and/or require low power.

The present invention contemplates the use of any regions of the electromagnetic spectrum which allow for analysis of the substrate 1000 and liquid 2000, as well as various techniques and sources for excitation in using the particular type of spectroscopy. The present invention also contemplates the use of other techniques and components for digital imaging to allow for use of chemical imaging of the substrate 1000 and liquid 2000. It should be further understood that dispensing confirmation system 500 also contemplates the use of surrogate detection in any of the spectral ranges.

The coating system 600 of machine 10 provides for a coating (not shown) to be placed on the substrate 1000 and/or over the liquid 2000, or some portion thereof. The coating 2300 may be a sealant or a protective layer. Coating system 600 has a coating device 610, a coating source 620 and a coating dryer 630 (if necessary depending upon the particular coating being used). The coating device 610 transfers the coating to the upper surface of the substrate 1000. A pad-printing device can be used for coating device 610 and is advantageous because of its efficient transfer of the coating to the substrate without any waste, e.g., no overspray. Alternative devices can also be used, such as, for example, a spray device (not shown) or ink jet device to spray the coating upon the substrate 1000. The spray device could also be movably connected to gantry 615 to pass over each of the substrate positions 220. The present invention contemplates the use of other devices and methods for applying a coating to the substrate 1000, such as, for example, an ultrasonic atomizer. The coating system 600 can use intermittent, low volume atomized sprayers to locally apply the coating over the all or a portion(s) of the surface of substrate 1000. The sprayer may use volumetric pumps to intermittently supply coating materials. A two fluid air-liquid atomization sprayer may also be used to generate a fine spray.

In the preferred embodiment of machine 10, coating device 610 is connected to or is positioned adjacent to the machine 10 to coat an array of substrates with each reciprocating stroke. Coating device 610 can be movably connected to a gantry 615 or other similar device to facilitate movement of the coating device with respect to the holding tray 220. The holding tray 220 continues to move as the coating is being applied by the coating device 610. However, the present invention contemplates the use of other devices and methods of positioning the coating device 610 with respect to each of the substrate positions 220 so that the coating is accurately applied.

The coating device 610 is releasably connected to the coating source 620. In the preferred embodiment of the machine 10, the coating source 620 is a movable container 625 that is connected to the coating device 610 via removably connectable conduit 627, so that the coating can be quickly and efficiently replaced.

As described above with respect to the dispensing of the substrate 1000 in layers or on opposing sides, the coating system can provide the necessary coating depending upon how the liquid 2000 has been added to the substrate, such as, for example, on both sides or between layers. This can facilitate the use of higher volumes of liquid 2000.

Coating dryer 630 can be used to perform drying of the coating (where appropriate) that has been applied to the substrate 1000 and/or over the liquid 2000. The coating dryer 630 preferably has an oven 640 and oven sensors 650 (not shown in detail). The oven 640 provides heat and air flow to the coating. The oven sensors 650, similar to the temperature conditioner sensors 482 discussed above, monitor the drying conditions of the coatings to ensure that the products meet the required tolerances.

The printing system 700 of machine 10 provides an identification marker on the substrate 1000. The printing system 700 preferably has a pad-printing device 710 that transfers the marker to the substrate 1000 and a pair of cameras 720 that obtain an image 730 of each of the identification markers to verify the quality of the image. Unacceptable substrates 1000 will be identified by the control system 900 for subsequent rejection by system 800.

In the preferred embodiment of machine 10, pad-printing device 710 and cameras or digital/video recording devices 720 are movably connected to a gantry 735 (similar to gantries 410, 510 and 615) to facilitate movement of the pad-printing device with respect to the holding tray 210 that continues to move as the identification marker is being applied. However, the present invention contemplates the use of other devices and/or methods, for positioning the pad-printing device 710 or alternative device with respect to each of the substrate positions 220 for accurate application of the identification markers, such as, for example, lasermarking, inkjet or rotogravure. Each of the marker images 730 is provided to control system 900 for inspection and to determine if the printed identification marker meets the required tolerances of the products. Also, the present invention contemplates machine 10 having an ink dryer (not shown), such as, for example, an oven, that applies heat and/or air-flow to the identification marker to dry it.

The acception-rejection system 800 provides products that have undergone real-time monitoring and adjustment for quality control to ensure that each of the products meets the required tolerances. Based upon the real-time monitoring being continuously performed at various stages of the process by machine 10, control system 900 has designated each and every product as either acceptable or rejected.

Acceptable products pass through to the delivery area (not shown in detail), preferably under bias that is selectively controlled by the control system 900, while rejected product drop into a scrap area, preferably under the force of gravity. However, the present invention contemplates the use of other structures and methods of separating those products that are designated by control system 900 as acceptable from those products that have been designated by the control system as rejected.

The control system 900 coordinates and synchronizes the various stages and systems of the machine 10. In the preferred embodiment, control system 900 is a distributed process control system that has a number of microprocessors 910 that control the different systems of machine 10. The microprocessors are preferably coordinated through a workstation 920. However, the present invention contemplates other types of system control including central and regional control, such as, for example, a single microprocessor 910 controlling all of the systems or similar systems being controlled by one of several microprocessors 910.

The microprocessors 910 and workstation 920 are in communication with each other, preferably through a network 930 using an Ethernet switch 935, which allows for the real-time monitoring, feedback and adjustment of the process being performed by the machine 10. The present invention contemplates the use of other structures and methods for communication, such as, for example, hardwiring. The control system 900 also has an archive microprocessor or historian 940, which is used to centrally store the large amount of data that is compiled for each and every product that is processed by the machine 10. However, the present invention contemplates other methods of storage of the process data, such as, for example, microprocessors 910 individually storing the data that they have compiled.

The control system 900 preferably has a number of monitors 950 that provide displays of the data, portions of the data, summaries of the data, and/or calculations and conclusions based upon the data, so that the workers can monitor and/or adjust the process as it is occurring. More preferably, the monitors 950, through use of the various microprocessors 910 and/or workstation 920, can selectively display the data, portions of the data, summaries of the data, calculations based upon the data, and conclusions based upon the data. Preferably, control system 900 records data for every product, which includes time, initial substrate status, droplet volume, temperature conditioner temperature, temperature conditioner humidity, temperature conditioner air flow, liquid location on substrate, liquid quantity and acceptability.

The present invention also contemplates dispensing inspection system 460 utilizing optical profilometry for real-time monitoring and feedback control. The components utilized by dispensing inspection system 460 to carry out the optical profilometry are known to one skilled in the art, such as, for example, a laser and camera. The technique of optical profilometry is especially useful for larger volumes of liquid 2000, such as, for example, greater than 10 ul, where the dispensing system 400 is dispensing a stream, as opposed to the droplet 2100.

For the optical profilometry technique, dispensing inspection system 460 performs a first scan of the substrate 1000 prior to dispensing of the liquid 2000 in order to obtain a first profile of the substrate. A second scan is then performed by the dispensing inspection system 460 to obtain a second profile of the substrate 1000 with the liquid 2000 thereon. The difference in the first and second profiles provides the measurement of the volume of liquid 2000 that has been dispensed onto the substrate 1000. The present invention further contemplates the use of optical profilometry of the substrate 1000 after the liquid 2000 has been dried on the substrate. Also, the first profile may be based upon a predetermined value for the same substrates 1000 to expedite the process and eliminate the need for two scans.

The present invention also contemplates the use of the real-time monitoring to provide real-time feedback and adjustment to the conveyor and dispensing systems 300 and 400, such as, for example, adjusting the speed for better positioning of the droplet 2100 on the substrate 1000 or adjusting the pump 425 and/or nozzle 450 to increase or decrease the volume of the droplet, which increases or decreases the amount of liquid 2000 that is ultimately dried on the substrate. The use of real-time monitoring of the droplet 2100 both before and after contact with the substrate 1000, also would allow for more efficient accounting for any losses occurring during the process.

Figure 4:
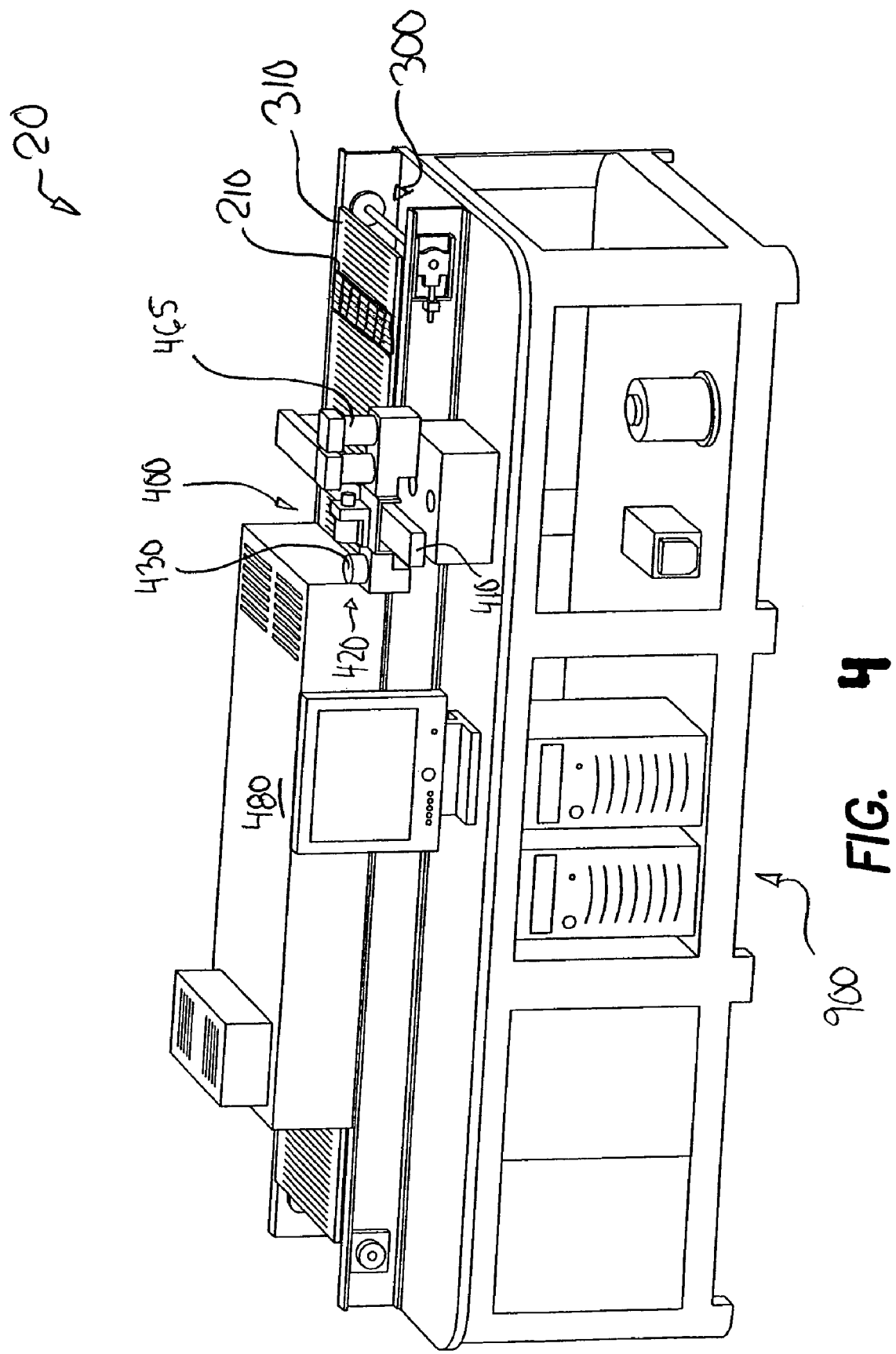
FIG. 4 is a perspective view of an alternative embodiment of a machine of the present invention.
Figure 6:
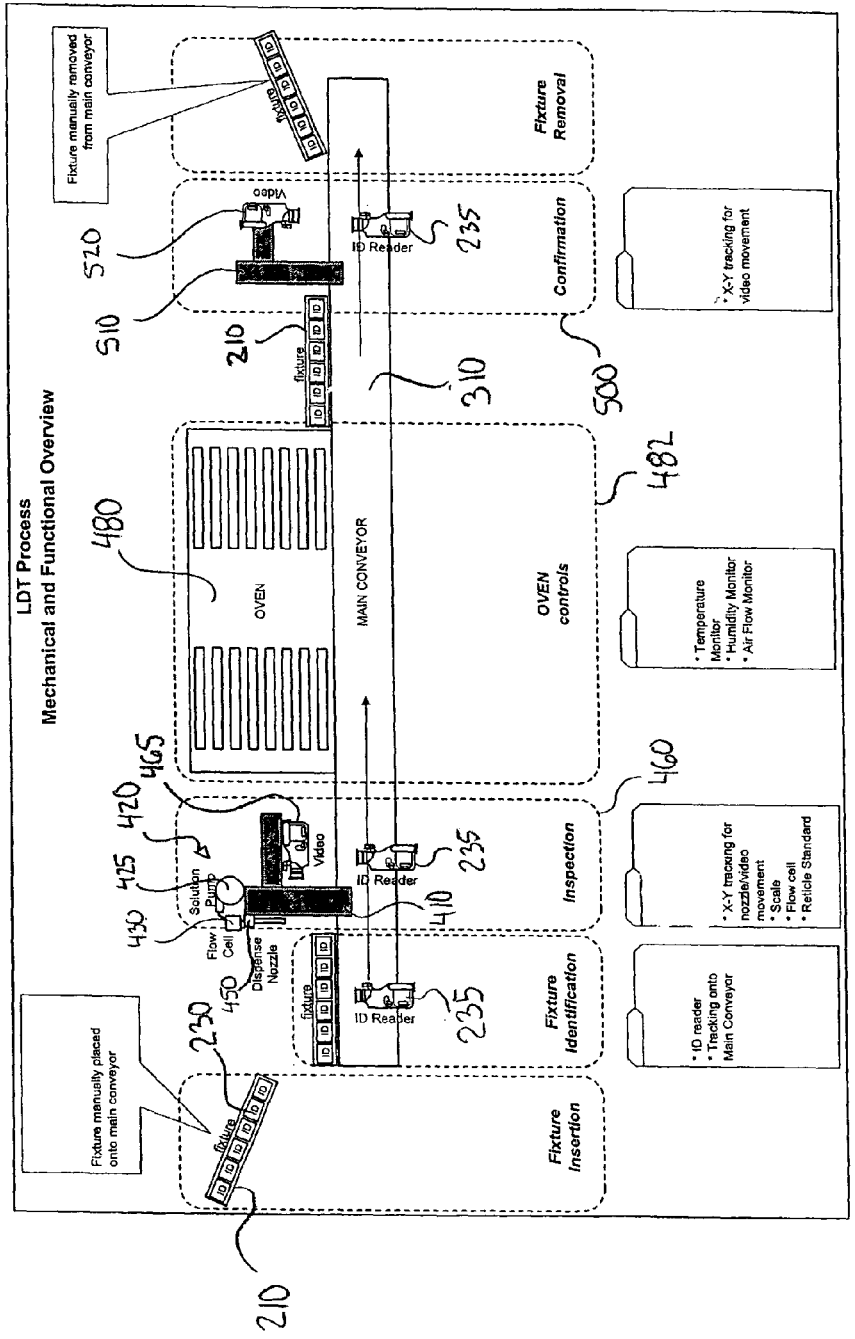
FIG. 6 is a schematic representation of components of the machine of FIG. 4.
Figure 7:
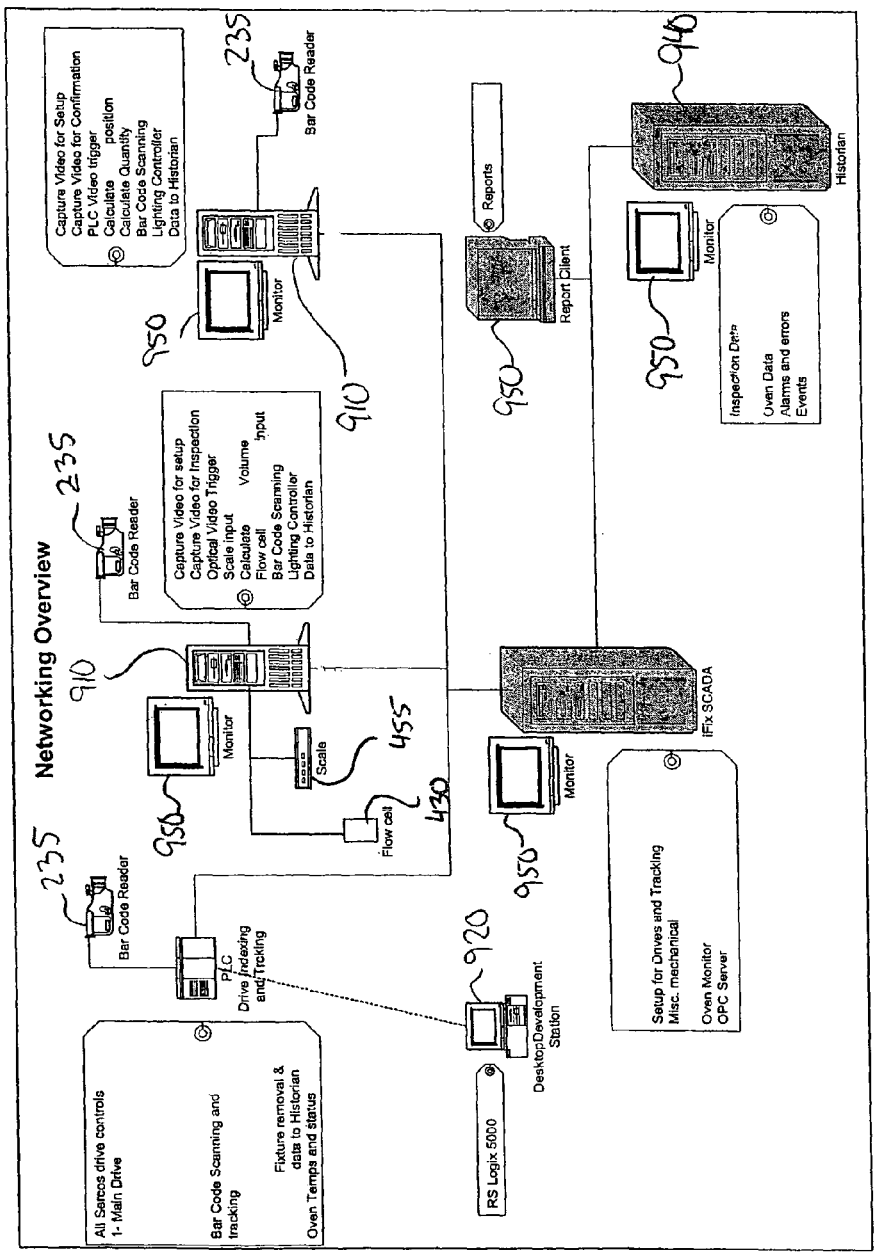
FIG. 7 is a schematic representation of the communication between the components of the machine of FIG. 4.

Referring to FIGS. 4, 6 and 7, another embodiment of an apparatus or machine of the present invention is shown and generally referred to by reference numeral 20. The machine 20 has components that are similar to the components described above with respect to the preferred embodiment of FIG. 1 and are similarly numbered, such as, conveyor system 300, dispensing system 400 and control system 900. Machine 20 is a scaled-down version of the preferred embodiment but still provides real-time monitoring for the process. Each of these systems 300, 400 and 900 are operably connected to each other to efficiently and ergonomically provide products that have each undergone real-time monitoring, and, preferably, real-time feedback and adjustment.

Holding trays 210 are manually placed on drive conveyor 310 where the substrates 1000 begin their descent through machine 20. Each holding tray 210 is identified through use of the bar code 230 on the tray and a scanner 235. The holding trays 210 continue to move along machine 20 and pass through to the dispensing system 400 where a dispensing module 420, which is mounted to gantry 410, dispenses droplets 2100 on each of the substrates 1000. Camera 465 takes an image of each droplet being dispensed and, in conjunction with the flow cell 430, the real-time monitoring of the amount of liquid being dispensed occurs.

After passing through temperature conditioner 480, where the liquid 2000 is formed on the outer surface or substantially along the outer surface of the substrate 1000, each of the substrates undergoes real-time monitoring of the position and amount of the liquid. Camera 520, which is mounted on gantry 510, obtains an image 525 of each of the substrates 1000 and liquids 2000 thereon. The images 525 are processed by control system 900 for the location and quantity of the liquid 2000.

Using spectroscopy, camera 520 captures the image 525 of the deposition spot left after dispensing and drying. Image analysis software uses gray scale to tabulate the number of pixels and relative intensity of the pixel to develop an image of the dried spot left behind. Based on this information, the amount of the liquid 2000 on the substrate 1000 is determined.

The holding tray 210 is then manually removed from the drive conveyor 310. Data has been compiled for each product regarding dispensing position, quantity of liquid 2000, and drying conditions. This data is used by control system 900 to provide a designation for each of the products as either acceptable or rejected. The machine 20 uses separate scanners 235 at different stages of the machine for identification of the individual substrates 1000.

Figure 5:
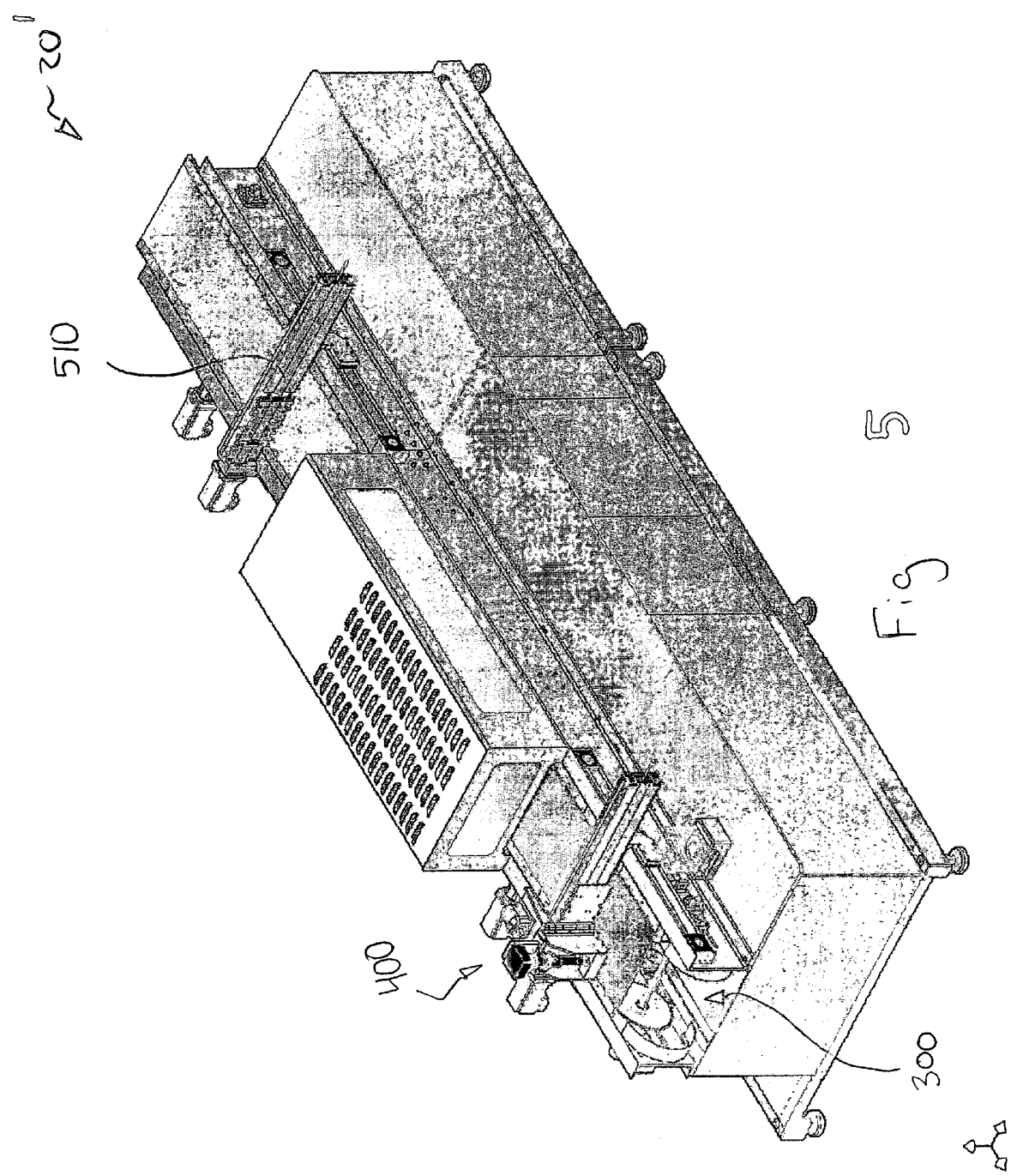
FIG. 5 is a perspective view of another alternative embodiment of a machine of the present invention.

A second alternative embodiment of the apparatus of the present invention is shown in FIG. 5 and is generally represented by reference numeral 20'. Similar to the embodiment described above with respect to FIGS. 4, 6 and 7, machine 20' is a scaled down version of the preferred embodiment of machine 10 shown in FIG. 1. Machine 20' has many features similar to machines 10 and 20 and such features are similarly numbered, such as, conveyor system 300, and dispensing system 400. Machine 20' exemplifies the modularity of the present invention as it includes the features of machine 20 and additionally has gantry 510, which is readily available for connection with dispensing confirmation system 500.

It should be further understood that some of the components and/or systems described with respect to machines 10, 20 and 20' may not need to be utilized for certain products. For example, but not limited to, products that are highly regulated may require rigorous quality control. Control system 900 will synchronize the other systems based upon the lack of use of certain systems, which will further maximize the efficiency of the process, such as, for example, where drying of substrate 1000 and liquid 2000 is minimal or not required, the other activities can be greatly sped up.

The present invention contemplates machines 10, 20 and 20', and the various components and systems therein, being modular. This will allow machines 10, 20 and 20' to carry out only the necessary activities for particular products by removing selected unnecessary components, and will provide time saving, such as, for example, avoiding passing holding trays 220 through the coating temperature conditioner 630 where no coating is being applied.

The present invention contemplates the interchangeability of different components to perform the various activities of machines 10, 20 and 20', such as, for example, probe 530 that performs chemical imaging being interchangeable with other probes that perform other types of analysis, such as, for example, spectroscopy and chemical imaging, such as, for example, utilizing Raman, UV reflectance, fluorescence, and/or terahertz. Machines 10, 20 and 20' can utilize the type of analysis, and hence the components that perform that analysis, which are most efficient and accurate for a particular product. The present invention also contemplates control system 900 indicating which types of analysis and their corresponding components are to be used for a particular product.

The present invention further contemplates the process performed by machines 10, 20 and 20' including a packaging step so that the end result is a product that is ready for shipping, especially where real-time release of products is utilized. The design and modularity of machines 10, 20 and 20' facilitates the addition of a packaging step to the process (where appropriate).

Machines 10, 20 and 20' also provide the ability to change production to a different product in a fraction of the time that it takes to make a similar adjustment to a contemporary machine. The cleaning of the machines 10, 20 and 20' for a change of production to a different product requires only the cleaning of the dispensing module 420, which can be quickly disassembled. Dispensing modules 420 are relatively low-cost which allows for their replacement rather than a time-consuming repair.

Machines 10, 20 and 20' improve efficiency in manufacturing the products based upon the manufacturing steps as well as the quality control steps. The continuity of the process quickly and efficiently provides the products that are directly ready for packaging, without the need for any other quality control testing being performed on them. Also, machines 10, 20 and 20' provide a process that can be run continuously without the need for stopping as in contemporary devices and techniques.

The real-time monitoring, feedback and adjustment of the present invention avoids unnecessary manufacturing steps (e.g., dispensing on rejected substrates) and provides quality control based on the individual properties of each of the substrates. The present invention is cost effective because it only discards the defective product identified by control system 900, rather than discarding all of the products in a batch that has a significant number of defective substrates, as by contemporary methods of product sampling.

The present invention contemplates the use of individual systems or combinations of systems of machines 10, 20 and 20' in combination with other devices, to provide one or more of the steps described herein. It should be further understood by one of ordinary skill in the art that the degree of real-time monitoring and/or feedback can be varied depending upon the particular product being manufactured and/or based upon other factors. For example, but not limited to, the machine 10, 20 and 20' may only utilize the high-speed imaging for detection of whether the droplet 2100 has accurately been dispensed upon carrier substrate 1000. Preferably, the volume calculation of dispensing inspection system 460 is also utilized to calculate the amount of liquid 2000 in the droplet 2100. However, the use of contemporary quality control techniques is also contemplated, such as batch sampling. Also, the present invention contemplates the use of contemporary quality control techniques, such as, for example, batch sampling, in parallel with the real-time monitoring and/or feedback described herein for machines 10, 20 and 20'.

It should be further understood by one of ordinary skill in the art that the various devices, techniques and/or systems described herein for machines 10, 20 and 20' can be utilized by themselves or in combination with one or more of the other systems of machines 10, 20 and 20' or in combination with contemporary devices for manufacturing products. For example, but not limited to, the high-speed imaging and volume calculation of dispensing inspection system 460 may be followed by a contemporary batch sampling technique for quality control of the resulting products.

The video imaging and volume calculation of dispensing inspection system 460 provides versatile real-time monitoring and feedback control for the products. This type of quality control is not dependent on the particular formulation of the liquid 2000, as opposed to some forms of chemical imaging which have such dependency.

It should also be noted that the terms "first", "second", "third", "fourth", "upper", "lower", and the like, are used herein to modify various elements. These modifiers do not imply a spatial, sequential, or hierarchical order to the modified elements unless specifically stated.

While the present invention has been described with reference to one or more exemplary embodiments, it will be understood by those skilled in the art that various changes may be made and equivalents may be substituted for elements thereof without departing from the scope of the present invention. In addition, many modifications may be made to adapt a particular situation or material to the teachings of the disclosure without departing from the scope thereof. Therefore, it is intended that the present invention not be limited to the particular embodiment(s) disclosed as the best mode contemplated, but that the invention will include all embodiments falling within the scope of the appended claims.

What is claimed is:

1. An apparatus for producing a product by dispensing a droplet of liquid on a carrier substrate, the apparatus comprising:
    a dispensing module for dispensing the droplet onto the carrier substrate;
    a device for moving the carrier substrate along a first axis of the apparatus;
    a first camera connected to said dispensing module;
    a mechanism operably connected to said first camera, wherein said mechanism actuates said first camera to obtain a first image of the droplet while the droplet is in-flight between said dispensing module and the carrier substrate;
    a processor in operative communication with said first camera, said processor determining an amount of the droplet based upon said first image; and
    a control system in communication with said device for moving the carrier substrate and said dispensing module, wherein said control system controls said device to move said carrier substrate continuously along said first axis as said first image is being obtained and as said dispensing module dispenses said dosage, and controls said dispensing module to move along said second axis as said dispensing module dispenses the droplet of liquid.

2. The apparatus of claim 1, wherein said dispensing module and said first camera are connected to a gantry, said gantry traversing said device for moving the carrier substrate, along said second axis.

3. The apparatus of claim 1, further comprising a probe that performs spectroscopy on the droplet after the droplet has been dispensed onto the carrier substrate.

4. The apparatus of claim 3, wherein the carrier substrate continues to move along said first axis as said probe performs said spectroscopy.

5. The apparatus of claim 3, wherein said spectroscopy is taken from the group consisting of near infrared, mid-infrared, ultraviolet/visible, fluorescence, laser induced fluorescence, Raman, terahertz, and any combinations thereof.

6. The apparatus of claim 1, further comprising a confirmation system having a second camera that obtains a second image of the droplet after the droplet has been dispensed onto the carrier substrate, wherein said confirmation system determines a position of the droplet on the carrier substrate based on said second image.

7. The apparatus of claim 6, wherein the carrier substrate continues to move along the apparatus as said second camera obtains said second image.

8. The apparatus of claim 1, further comprising a temperature conditioning system that changes a temperature of the droplet after it has been dispensed onto the carrier substrate, to facilitate formation of the droplet on the carrier substrate.

9. The apparatus of claim 8, wherein said temperature conditioning system monitors environmental parameters for the carrier substrate, and wherein the environmental parameters are taken from the group consisting of temperature, air-flow rate, humidity, radiation, product surface temperature, and any combinations thereof.

10. The apparatus of claim 1, further comprising a printing system for applying an identification marker to the carrier substrate, and a third camera for obtaining a third image of said identification marker for inspection.

11. The apparatus of claim 1, wherein the carrier substrate continues to move along the apparatus as said third camera obtains said third image.

12. The apparatus of claim 1, further comprising a control system for performing real-time control of said dispensing of the droplet, wherein said real-time control comprises adjusting said amount of the droplet.

13. The apparatus of claim 1, wherein said dispensing module has a nozzle for dispensing the droplet.

14. The apparatus of claim 13, further comprising a control system for performing real-time control, and wherein said real-time control comprises adjusting a position of said nozzle with respect to the carrier substrate, thereby adjusting the position of the droplet on the carrier substrate.

15. An apparatus for producing a product having a carrier substrate and a droplet of liquid dispensed thereon, the system comprising:
    a dispensing module for dispensing the droplet onto the carrier substrate;
    a device for moving the carrier substrate along a first axis of the apparatus;
    a confirmation system operably connected to the apparatus, said confirmation system determining an amount of the droplet after the droplet has been dispensed onto the carrier substrate, wherein said confirmation system performs optical profilometry on the carrier substrate to determine the amount of the droplet; and
    a control system in communication with said device for moving the carrier substrate and said dispensing module, wherein said control system controls said device to move said carrier substrate continuously along said first axis as said confirmation system performs said optical profilometry, and controls said dispensing module to move along said second axis as said dispensing module dispenses the droplet of liquid.

16. The apparatus of claim 15, wherein said dispensing module moves along a second axis of the apparatus as said dispensing module dispenses the droplet, wherein said second axis is traverse to said first axis.

17. A method of producing a product that has a carrier substrate and a droplet of liquid dispensed thereon, the method comprising:

dispensing the droplet onto the carrier substrate;
obtaining a first image of the droplet while the droplet is in-flight onto the carrier substrate;
determining an amount of the droplet based upon said first image; and
controlling said carrier substrate to move continuously as said first image is being obtained and as said dosage is dispensed.

18. The method of claim 17, wherein the droplet is dispensed by a dispensing module that moves along a second axis of the apparatus, and said controlling step further comprises controlling said dispensing module to move along said second axis as said dispensing module dispenses the droplet of liquid.

19. The method of claim 17, further comprising performing spectroscopy on the droplet after it has been dispensed onto the carrier substrate.

20. The method of claim 19, further comprising continuously moving the carrier substrate along said first axis of the apparatus as said spectroscopy is being performed.

21. The method of claim 17, further comprising:
obtaining a second image of the droplet after it has been dispensed onto the carrier substrate, and
determining a position of the droplet on the carrier substrate, based on said second image.

22. The method of claim 21, further comprising continuously moving the carrier substrate along said first axis of the apparatus as said second image is being obtained.

23. The method of claim 22, further comprising changing a temperature of the droplet after it has been dispensed onto the carrier substrate, to facilitate formation of the droplet on the carrier substrate.

24. The method of claim 23, further comprising applying an identification marker to the carrier substrate.

25. The method of claim 24, further comprising obtaining a third image of said identification marker for inspection.

26. The method of claim 25, further comprising continuously moving the carrier substrate along said first axis of the apparatus as said third image is being obtained.

* * * * *

UNITED STATES PATENT AND TRADEMARK OFFICE
Certificate

Patent No. 8,101,244 B2                                                                                      Patented: January 24, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Allan J. Clarke, Collegeville, PA (US); David George Doughty, Harlow (GB); Frederick H. Fiesser, King of Prussia, PA (US); David Tainsh, Middlesex (GB); Dwight Walker, Research Triangle Park, NC (US); and David Wagner, Research Triangle Park, NC (US).

Signed and Sealed this Thirteenth Day of March 2012.

<div align="right">

PHILIP C. TUCKER
*Supervisory Patent Examiner*
Art Unit 1745
Technology Center 1700

</div>